(12) United States Patent
Ushiroda et al.

(10) Patent No.: US 12,045,979 B2
(45) Date of Patent: Jul. 23, 2024

(54) MEDICAL IMAGE PROCESSING DEVICE AND MEDICAL OBSERVATION SYSTEM

(71) Applicant: Sony Olympus Medical Solutions Inc., Tokyo (JP)

(72) Inventors: Hiroshi Ushiroda, Tokyo (JP); Koji Fukaya, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 216 days.

(21) Appl. No.: 17/547,233

(22) Filed: Dec. 10, 2021

(65) Prior Publication Data

US 2022/0245796 A1 Aug. 4, 2022

(30) Foreign Application Priority Data

Jan. 29, 2021 (JP) .................... 2021-012606

(51) Int. Cl.
*G06T 7/00* (2017.01)
*A61B 90/00* (2016.01)
*G09G 3/20* (2006.01)

(52) U.S. Cl.
CPC ............ *G06T 7/0012* (2013.01); *A61B 90/37* (2016.02); *G09G 3/2092* (2013.01); *G06T 2207/30041* (2013.01); *G09G 2320/0626* (2013.01); *G09G 2320/0666* (2013.01); *G09G 2340/125* (2013.01)

(58) Field of Classification Search
CPC .................. A61B 90/37; G06T 7/0012; G06T 2207/30041; G09G 3/2092; G09G 2320/0626; G09G 2320/0666; G09G 2340/125
USPC ........................................................ 345/629
See application file for complete search history.

(56) References Cited

U.S. PATENT DOCUMENTS

| | | | |
|---|---|---|---|
| 2004/0102799 A1* | 5/2004 | Perez ..................... | A61B 90/36 606/166 |
| 2006/0247659 A1* | 11/2006 | Moeller ................. | A61B 3/113 606/107 |
| 2016/0354241 A1* | 12/2016 | Mordaunt ............. | A61F 9/0084 |
| 2019/0313902 A1* | 10/2019 | Charles ................ | A61B 3/0025 |
| 2020/0252554 A1* | 8/2020 | Themelis ............. | H04N 5/2621 |

FOREIGN PATENT DOCUMENTS

WO 2017/065018 A1 4/2017

* cited by examiner

*Primary Examiner* — Jacinta M Crawford
(74) *Attorney, Agent, or Firm* — XSENSUS LLP

(57) ABSTRACT

A medical image processing device includes: image acquisition unit configured to acquire image information obtained by imaging with a medical observation device; and superimposed image generation circuitry configured to generate a superimposed image in which a pattern image having first images with a specific shape arranged in parallel in a specific pattern and a captured image based on the image information are superimposed on each other.

17 Claims, 20 Drawing Sheets

FIG.20A  FIG.20C  FIG.20E
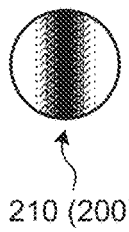  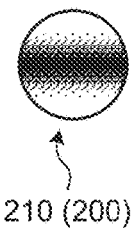
210 (200)  210 (200)  210 (200)  210 (200)  210 (200)  210 (200)
FIG.20B  FIG.20D  FIG.20F
FIG.21A  FIG.21C  FIG.21E
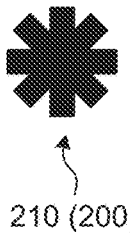 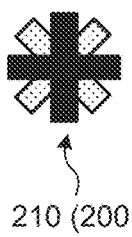 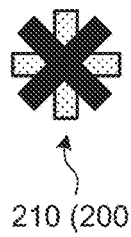 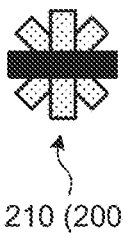 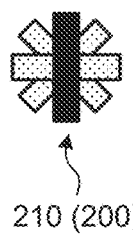 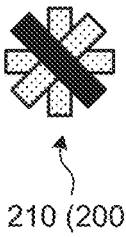
210 (200)  210 (200)  210 (200)  210 (200)  210 (200)  210 (200)
FIG.21B  FIG.21D  FIG.21F
FIG.21G  FIG.21I  FIG.21K
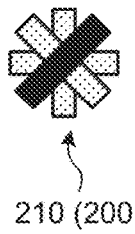 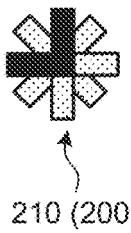 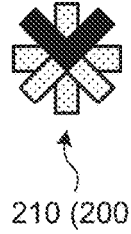 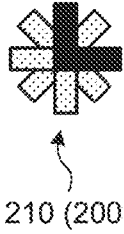 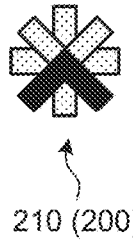
210 (200)  210 (200)  210 (200)  210 (200)  210 (200)
FIG.21H  FIG.21J

MEDICAL IMAGE PROCESSING DEVICE AND MEDICAL OBSERVATION SYSTEM

CROSS-REFERENCE TO RELATED APPLICATION

This application claims priority from Japanese Application No. 2021-012606, filed on Jan. 29, 2021, the contents of which are incorporated by reference herein in its entirety.

BACKGROUND

The present disclosure relates to a medical image processing device and a medical observation system.

A medical observation system has been known which is used for eye surgery such as cataract surgery (see, for example, WO 2017/065018 A).

According to a medical observation system described in WO 2017/065018 A, a captured image obtained by capturing an image of a subject eye with an imaging device is displayed in a display device. Then, a surgeon performs surgery while confirming the captured image displayed in the display device.

SUMMARY

In the meantime, since an affected part is biomedical tissue, there are few landmarks that may be used as a reference during surgery. Therefore, even if the surgeon confirms the captured image displayed in the display device during surgery, it is difficult to determine how much the hand holding a surgical tool should be moved to move the surgical tool in the captured image.

There is a need for a technique with which the amount of motion of the hand holding the surgical tool may be easily compared with the amount of movement of the surgical tool in the captured image, so as to improve convenience.

According to one aspect of the present disclosure, there is provided a medical image processing device including: image acquisition unit configured to acquire image information obtained by imaging with a medical observation device; and superimposed image generation circuitry configured to generate a superimposed image in which a pattern image having first images with a specific shape arranged in parallel in a specific pattern and a captured image based on the image information are superimposed on each other.

BRIEF DESCRIPTION OF THE DRAWINGS

FIGS. 20A to 20F are diagrams illustrating modifications to the first through sixth and the eighth through tenth embodiments; and FIGS. 21A to 21K are diagrams illustrating modifications to the first through tenth embodiments.

DETAILED DESCRIPTION

Hereinafter, modes for carrying out the present disclosure (embodiments below) will be described with reference to the drawings. Note that the present disclosure is not limited to the embodiments described below. Further, the same parts are denoted by the same reference signs when the drawings are described.

First Embodiment

Schematic Configuration of Medical Observation System

Figure 1:
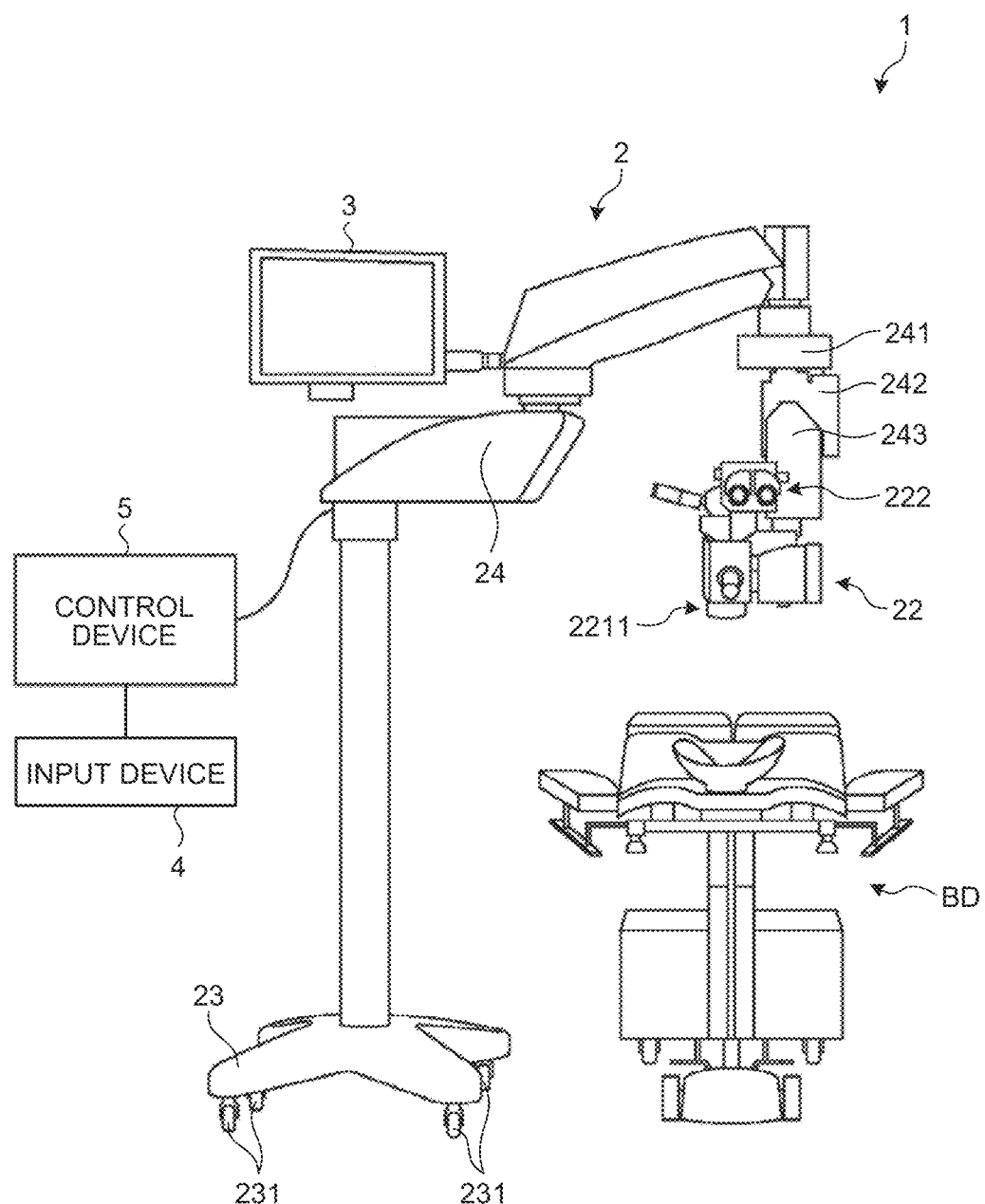
FIG. 1 is a diagram for explanation of a configuration of a medical observation system according to a first embodiment.
Figure 2:
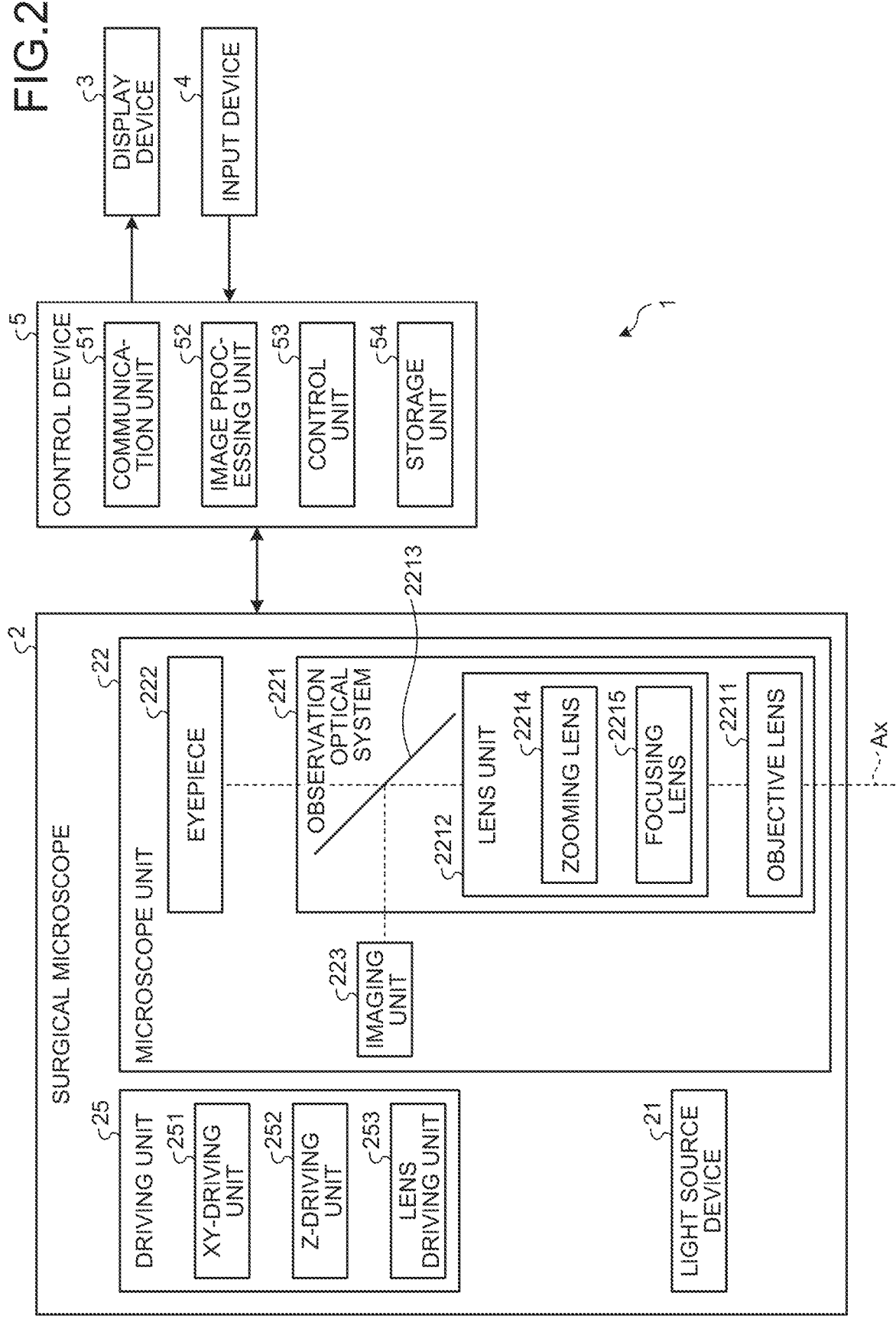
FIG. 2 is a diagram for explanation of a configuration of the medical observation system according to the first embodiment.

FIGS. 1 and 2 are diagrams for explanation of a configuration of a medical observation system 1 according to the first embodiment. Specifically, FIG. 1 is a diagram illustrating an external configuration of the medical observation system 1. FIG. 2 is a block diagram illustrating a configuration of the medical observation system 1.

The medical observation system 1 is a system used for surgery on an eye of a patient who lies on a patient bed BD (FIG. 1), the eye being hereinafter referred to as a "subject eye". As illustrated in FIG. 1 or FIG. 2, the medical observation system 1 includes a surgical microscope 2, a display device 3, an input device 4, and a control device 5.

The surgical microscope 2 corresponds to a medical observation device according to the present disclosure. Under the control of the control device 5, an image of the subject eye is captured. As illustrated in FIG. 1 or FIG. 2, the surgical microscope 2 includes a light source device 21 (FIG. 2), a microscope unit 22, a base unit 23 (FIG. 1), a supporting unit 24 (FIG. 1), and a driving unit 25 (FIG. 2).

The light source device 21 supplies, under the control of the control device 5, illumination light to illuminate the subject eye.

As illustrated in FIG. 1 or FIG. 2, the microscope unit 22 includes an observation optical system 221 (FIG. 2), an eyepiece 222, and an imaging unit 223 (FIG. 2).

The observation optical system 221 includes an objective lens 2211 (FIG. 1, FIG. 2), a lens unit 2212 (FIG. 2), and a half mirror 2213 (FIG. 2), and guides light reflected from the subject eye to the eyepiece 222 and the imaging unit 223. To be specific, the light reflected from the subject eye enters the half mirror 2213 through the objective lens 2211 and the lens unit 2212. The approximately half of the light that has entered the half mirror 2213 passes through the half mirror 2213 to enter the eyepiece 222. On the other hand, the other half of the light that has entered the half mirror 2213 is reflected on the half mirror 2213 to enter the imaging unit 223.

Here, as illustrated in FIG. 2, the lens unit 2212 includes a zooming lens 2214 and a focusing lens 2215.

The zooming lens 2214 is formed by use of one or a plurality of lenses, and moves along an optical axis Ax (FIG. 2) to adjust the angle of view. The optical axis Ax extends in the vertical direction of FIG. 1, and the optical axis Ax is the axis from the microscope unit 22 toward the subject eye.

The focusing lens 2215 is formed by use of one or a plurality of lenses, and moves along the optical axis Ax to adjust the focus.

The lens unit 2212 also includes an optical zooming mechanism (not illustrated) for moving the zooming lens 2214 along the optical axis Ax and a focusing mechanism (not illustrated) for moving the focusing lens 2215 along the optical axis Ax.

The eyepiece 222 condenses the light incident from the observation optical system 221 to form an optical image of the subject eye. This allows the surgeon who looks through the eyepiece 222 to observe the optical image of the subject eye.

The imaging unit 223 includes an image sensor such as a charge coupled device (CCD) or a complementary metal oxide semiconductor (CMOS) that receives the light incident from the observation optical system 221 and converts the light into an electric signal. The imaging unit 223 then outputs, under the control of the control device 5, a pixel signal (RAW signal or image signal, for example) obtained by image-capturing to the control device 5. The pixel signal corresponds to image information according to the present disclosure.

The base unit 23 is a base of the surgical microscope 2, and is formed to be movable on a floor surface via casters 231 (FIG. 1).

The supporting unit 24 extends from the base unit 23, and supports the microscope unit 22 at a distal end thereof (end away from the base unit 23). As illustrated in FIG. 1, the supporting unit 24 includes an XY-stage 241, an XY-moving unit 242, and a Z-moving unit 243.

The XY-stage 241 supports the XY-moving unit 242 so that the XY-moving unit 242 may move in the X-direction and in the Y-direction. Here, the X-direction and the Y-direction are along a plane orthogonal to the optical axis Ax and are orthogonal to each other.

The XY-moving unit 242 is a part movable in the X-direction and in the Y-direction with respect to the XY-stage 241. The XY-moving unit 242 supports the Z-moving unit 243 so that the Z-moving unit 243 may move in the Z-direction. Here, the Z-direction is along the optical axis Ax (the vertical direction in FIG. 1) and is orthogonal to the X-direction and the Y-direction.

The Z-moving unit 243 is a part movable in the Z-direction with respect to the XY-moving unit 242. The Z-moving unit 243 supports the microscope unit 22.

To be specific, the microscope unit 22 may be moved in the X-direction and in the Y-direction by operating the XY-moving unit 242. Further, the microscope unit 22 may be moved in the Z-direction by operating the Z-moving unit 243.

As illustrated in FIG. 2, the driving unit 25 includes an XY-driving unit 251, a Z-driving unit 252, and a lens driving unit 253.

The XY-driving unit 251 is an actuator such as a motor, and under the control of the control device 5, the XY-driving unit 251 operates the XY-moving unit 242 and moves the microscope unit 22 in the X-direction and in the Y-direction.

The Z-driving unit 252 is an actuator such as a motor, and under the control of the control device 5, the Z-driving unit 252 operates the Z-moving unit 243 and moves the microscope unit 22 in the Z-direction.

The lens driving unit 253 is an actuator such as a motor, and under the control of the control device 5, the lens driving unit 253 operates the optical zooming mechanism (not illustrated) or the focusing mechanism (not illustrated) to adjust the angle of view or the focus.

The display device 3 is formed by a display using liquid crystal, organic electro luminescence (EL), or the like, and under the control of the control device 5, the display device 3 displays an image based on a video signal from the control device 5.

The input device 4 is formed by use of an operational device such as a mouse, a keyboard, and a touch panel, and receives user operation from a user such as a surgeon. The input device 4 then outputs an operation signal according to the user operation to the control device 5.

The control device 5 corresponds to a medical image processing device according to the present disclosure. The control device 5 collectively controls the operation of the surgical microscope 2 and the display device 3. As illustrated in FIG. 2, the control device 5 includes a communication unit 51, an image processing unit 52, a control unit 53, and a storage unit 54.

The communication unit 51 is an interface for communication with the surgical microscope 2, and receives a pixel signal from the imaging unit 223 and sends a control signal received from the control unit 53. In other words, the communication unit 51 corresponds to an image acquisition unit according to the present disclosure.

The image processing unit 52 performs image processing on the pixel signal received by the communication unit 51 to generate a captured image based on the pixel signal, generates a video signal for display with which to display an image for display according to the captured image in the display device 3, and outputs the video signal to the display device 3.

Here, examples of the image processing include digital gain processing of multiplying the pixel signal (digital signal) received by the communication unit 51 by a digital gain for amplifying the digital signal, optical black subtraction processing, white balance (WB) adjustment processing, demosaic processing, color matrix calculation processing, gamma correction processing, YC conversion processing of generating a luminance signal and a color difference signal (Y, Cb/Cr signal), enlargement processing (electronic zoom), and the like.

The image processing unit 52 has functions of a pattern image generation unit, a superimposed image generation unit, and a display controller according to the present disclosure. The functions of the pattern image generation unit, the superimposed image generation unit, and the display controller are described in "operation of control device" later.

The control unit 53 is implemented by, for example, a central processing unit (CPU), a field-programmable gate array (FPGA), and the like, controls the operation of the surgical microscope 2 and the display device 3, and controls the entire operation of the control device 5. The control unit 53 has a function of a pattern image controller according to the present disclosure. The function of the pattern image controller is described in "operation of control device" later. Further, the control unit 53 may be configured, for example, as an IP converter having an image processing function. In such a case, the control unit 53 functions as an IP converter on the video source side that performs IP conversion on a video outputted from the surgical microscope 2 (video source) and sends the resultant over a network. The display device 3 is provided with an IP converter on the video output side that converts the video sent via the network into a format unique to the display device 3, and outputs the resultant. The IP converter on the video source side functions as an encoder, and the IP converter on the video output side functions as a decoder.

The storage unit 54 stores programs executed by the control unit 53, information necessary for the processing of the control unit 53, and so on.

About Cataract Surgery

Before the operation of the control device 5 is described, a brief description of the cataract surgery is given.

In the cataract surgery, the surgeon performs a port creation step, an anterior capsulotomy step, a hydrodissection step, a crystalline lens nucleus treatment step, and an intraocular lens insertion step in the stated order.

In the port creation step, the surgeon incises a cornea of the subject eye with a knife to define a port (incision).

The anterior capsulotomy step is called a continuous curvilinear capsulorrhexis (CCC) step. In the anterior capsulotomy step, the surgeon inserts tweezers with a pointed distal end through the port defined in the port creation step and incises the anterior portion of the crystalline lens, that is, the anterior capsule portion in a circular shape.

In the hydrodissection step, the surgeon inserts the distal end of the cannula between the crystalline lens capsule (the skin surrounding the crystalline lens) and the crystalline lens cortex through the port defined in the port creation step. The surgeon then makes perfusate flow through the cannula. This separates the crystalline lens capsule and the crystalline lens cortex from each other.

In the crystalline lens nucleus treatment step, the surgeon inserts a suction tube through the port defined in the port creation step. The surgeon then performs emulsification (pulverization) and aspiration of the nucleus of the crystalline lens through the suction tube by ultrasonic vibration called nucleus treatment, and also aspirates the cortex.

In the intraocular lens insertion step, the surgeon places an intraocular lens in a cartridge. The surgeon then inserts the cartridge through the port defined in the port creation step, and pushes the intraocular lens out of the cartridge and inserts the same into the subject eye.

Operation of Control Device

The description goes on to the operation of the control device 5. Hereinafter, the cataract surgery is taken as an example and the description is provided mainly of the functions of the pattern image generation unit, the superimposed image generation unit, and the display controller of the image processing unit 52 and the function of the pattern image controller of the control unit 53.

Figure 3:
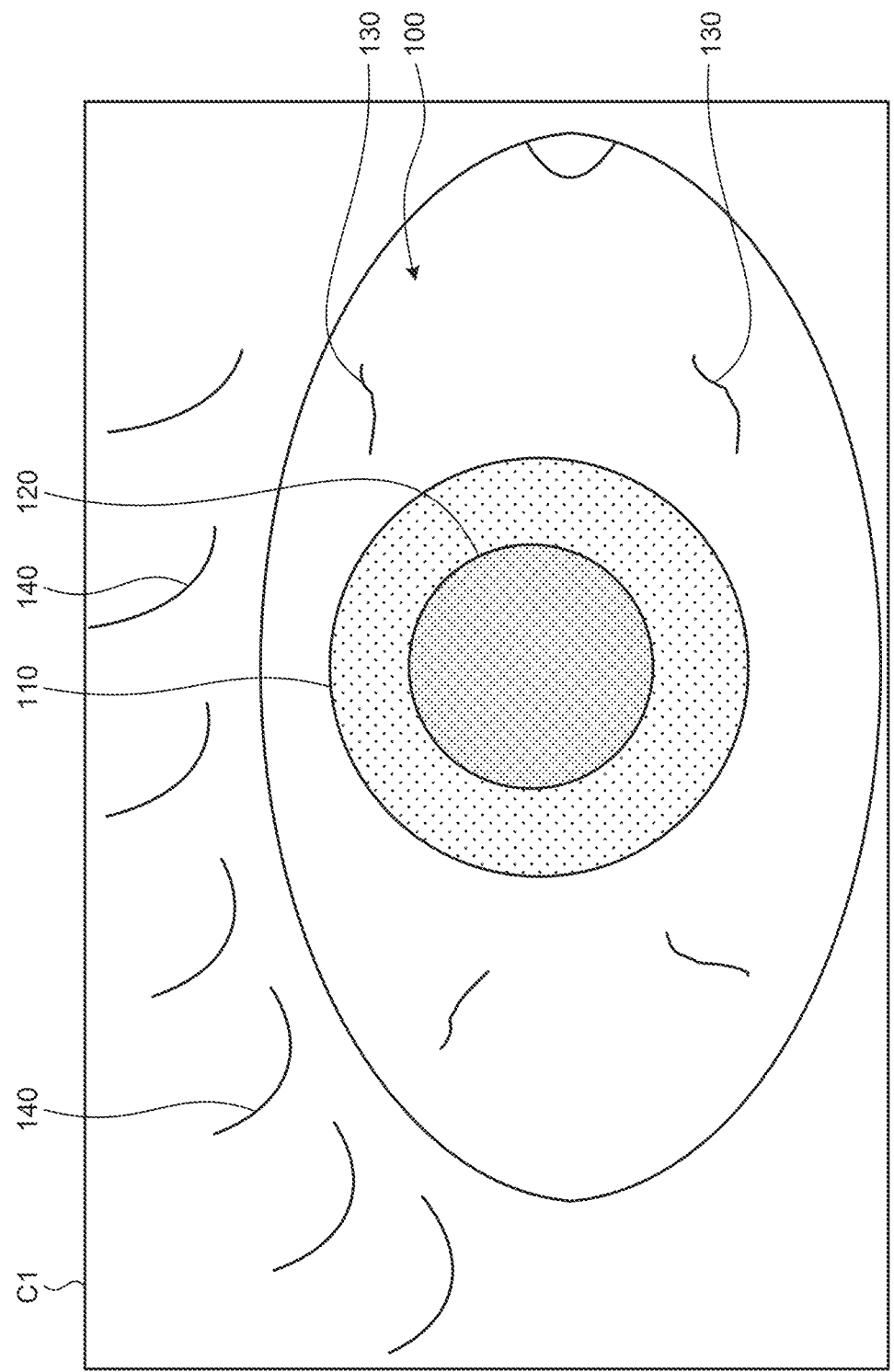
FIG. 3 is a diagram illustrating a captured image.
Figure 4:
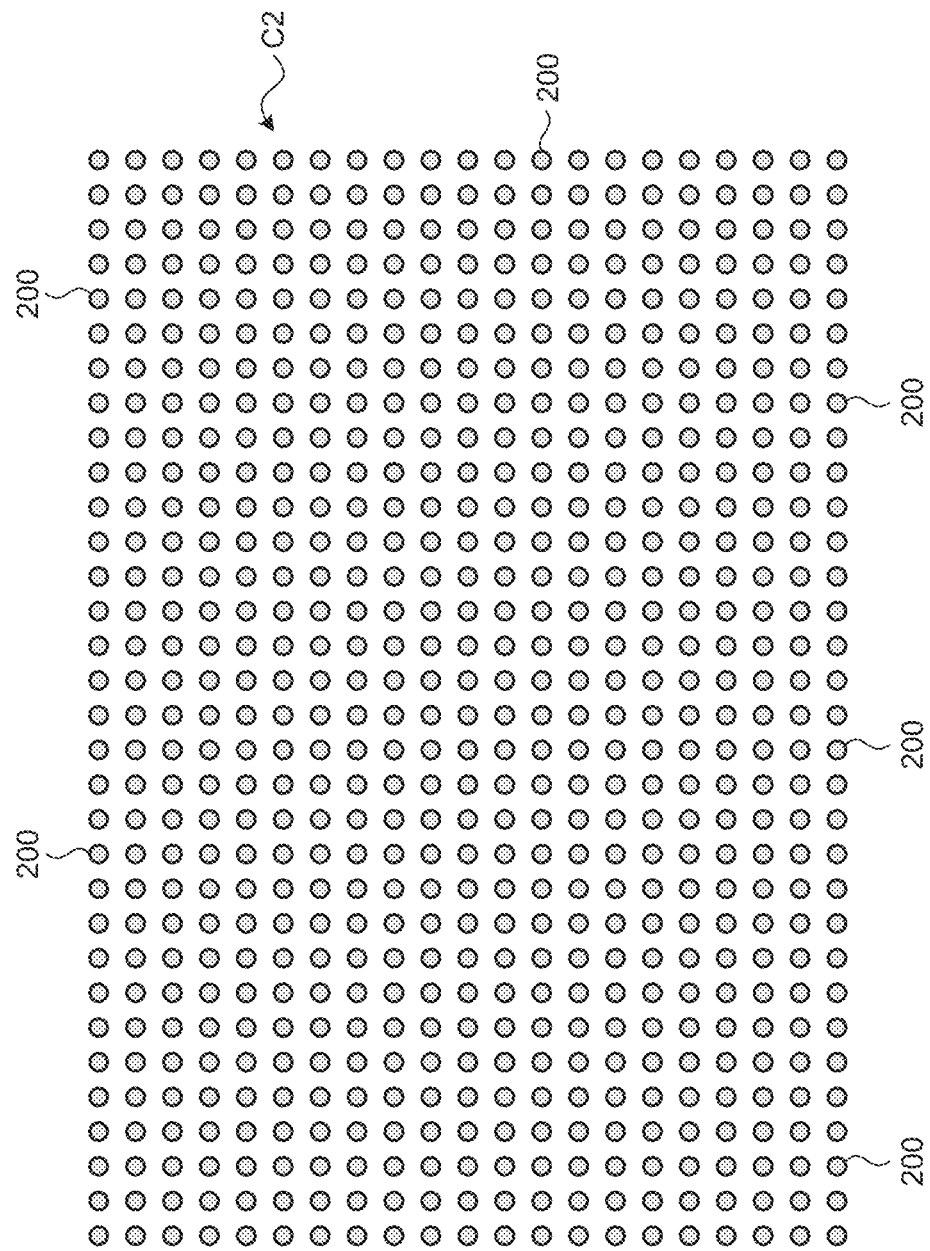
FIG. 4 is a diagram illustrating a pattern image.
Figure 5:
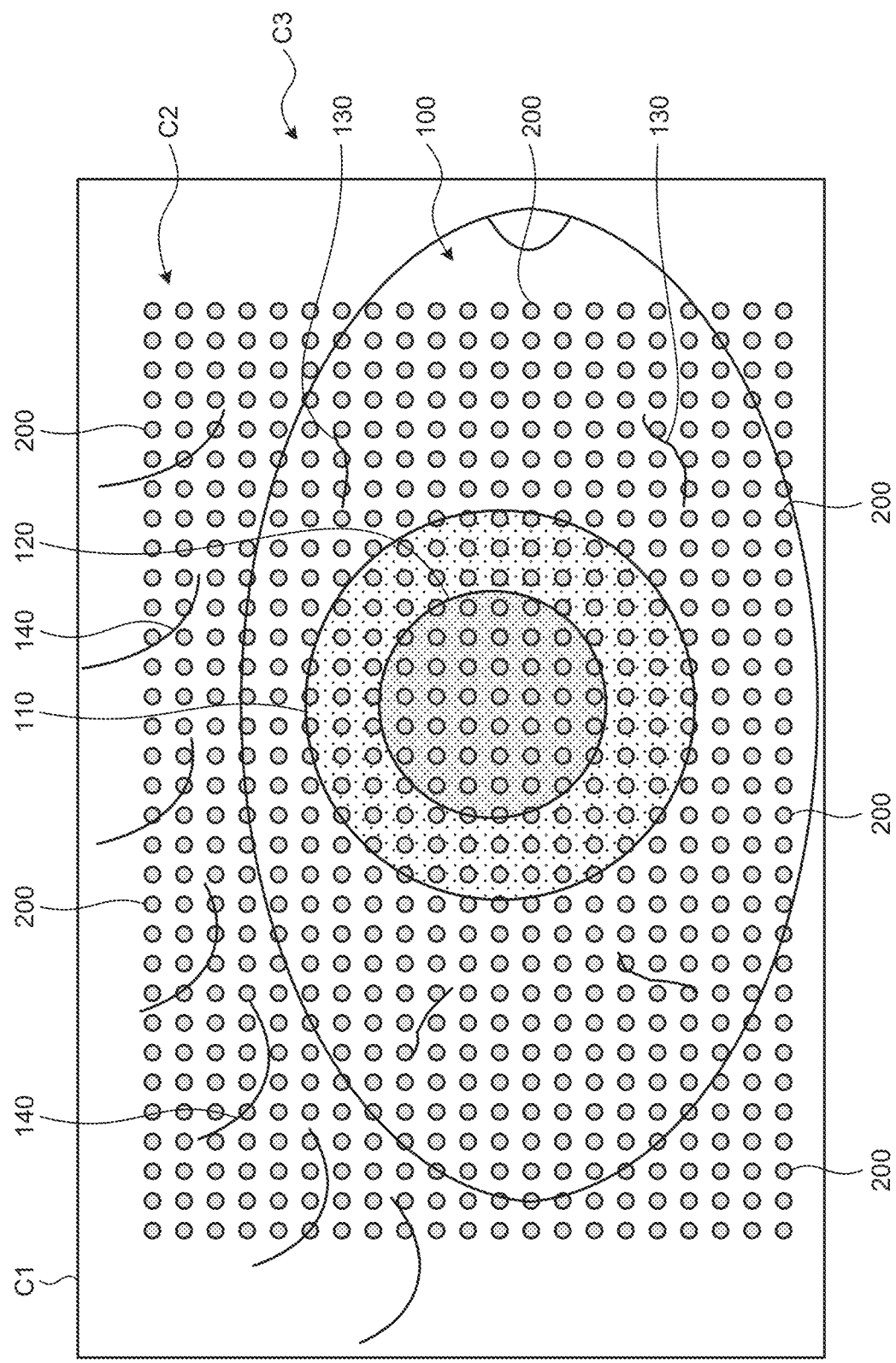
FIG. 5 is a diagram illustrating a superimposed image.
Figure 6:
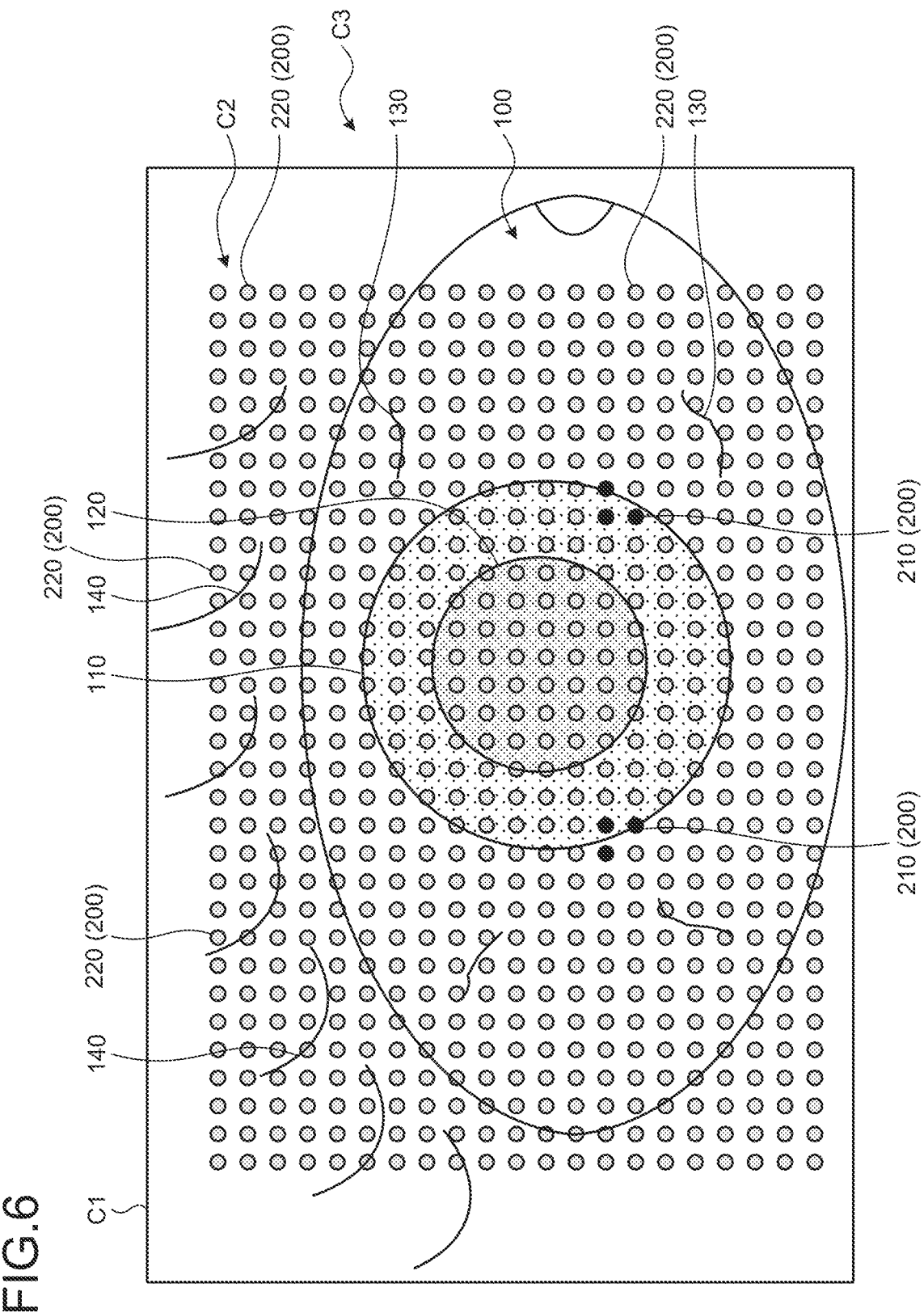
FIG. 6 is a diagram illustrating a superimposed image.

FIG. 3 is a diagram illustrating a captured image C1. FIG. 4 is a diagram illustrating a pattern image C2. FIGS. 5 and 6 are diagrams illustrating a superimposed image C3. In FIGS. 3, 5, and 6, the reference sign "100" indicates the subject eye. In addition, the reference sign "110" indicates the cornea. Further, the reference sign "120" indicates a pupil. The reference sign "130" indicates a blood vessel of sclera. The reference sign "140" indicates eyelashes.

The image processing unit 52 (pattern image generation unit) generates the pattern image C2 (FIG. 4) under the control of the control unit 53 (pattern image controller).

Here, the pattern image C2 is an image in which first images 200 having a specific shape are arranged in parallel in a specific pattern. In the first embodiment, the first image 200 is a circular dot as illustrated in FIG. 4. The pattern image C2 is an image in which the plurality of first images 200 are arranged in parallel at specific intervals in the vertical and horizontal directions.

Further, the image processing unit 52 (superimposed image generation unit) generates the superimposed image C3 (FIG. 5) in which the pattern image C2 generated as described above and the captured image C1 (FIG. 3) that is generated by the imaging unit 223 on the basis of a pixel signal acquired via the communication unit 51 are superimposed on each other.

Further, the image processing unit 52 (display controller) uses the superimposed image C3 generated described above as an image for display. The image processing unit 52 (display controller) then generates a video signal for display with which to display the image for display (superimposed image C3) in the display device 3, and outputs the video signal to the display device 3.

The control unit 53 (pattern image controller) controls the operation of the image processing unit 52 (pattern image generation unit) to generate the pattern image C2 (FIG. 6) as described below.

As illustrated in FIG. 6, the control unit 53 (pattern image controller) performs control to generate the pattern image C2 in which partial first images 210 of all the first images 200 in the pattern image C2 may be distinguished from the other first images 220. In the first embodiment, the control unit 53 (pattern image controller) performs control to generate the pattern image C2 in which the partial first images 210 may be distinguished from the other first images 220 by changing the overall appearance of the partial first images 210 without changing the shape (circular shape) of each of the first images 200. Specifically, the control unit 53 (pattern image controller) performs control to generate the pattern image C2 in which the partial first images 210 may be distinguished from the other first images 220 by changing at least one of the brightness and color of the partial first images 210 and transmittance to the captured image C1. Note that, in FIG. 6, the partial first images 210 are represented by dots painted in black, and the other first images 220 are represented by dots painted in gray, for convenience of explanation.

The control unit 53 (pattern image controller) selects the partial first images 210 from among all the first images 200 in the pattern image C2 as described below.

A patient who is to undergo cataract surgery has a preoperative examination before the cataract surgery. In the preoperative examination, an image of the subject eye of the patient is captured, and a captured image similar to the captured image C1 (hereinafter, referred to as a preoperative image) is generated. The surgeon or the like who performs the cataract surgery confirms the preoperative image displayed in the display device and identifies, in the preoperative image, an area serving as a specific indicator for performing the cataract surgery. Examples of the area serving as a specific indicator include an area indicating the position of a port to be incised in the port creation step, a circular area indicating an anterior portion to be incised in the anterior capsulotomy step, an area indicating the position of the astigmatism axis used in the intraocular lens insertion step, and an area indicating the center position of the subject eye.

The control unit 53 (pattern image controller) finds out a positional relationship between corresponding pixels of the preoperative image and the captured image C1 on the basis of at least one of structural features of the subject eye 100 included in the preoperative image and the captured image C1, for example, the contour of the pupil 120, the contour of the cornea 110 (the contour of an iris), the pattern of the iris, and the shape of the blood vessel 130 of the sclera. Further, the control unit 53 (pattern image controller) extracts, from the captured image C1, an area corresponding to the area identified in the preoperative image as described above (area serving as a specific indicator) (extracts an area having a specific feature in the captured image C1). The control unit 53 (pattern image controller) then uses the first images 200 located at a position corresponding to the extracted area in the pattern image C2 (within the extracted area, for example) as the partial first images 210. Note that FIG. 6 exemplifies a case where the area serving as a specific indicator is an area indicating the position of a port to be incised in the port creation step.

Figure 7:
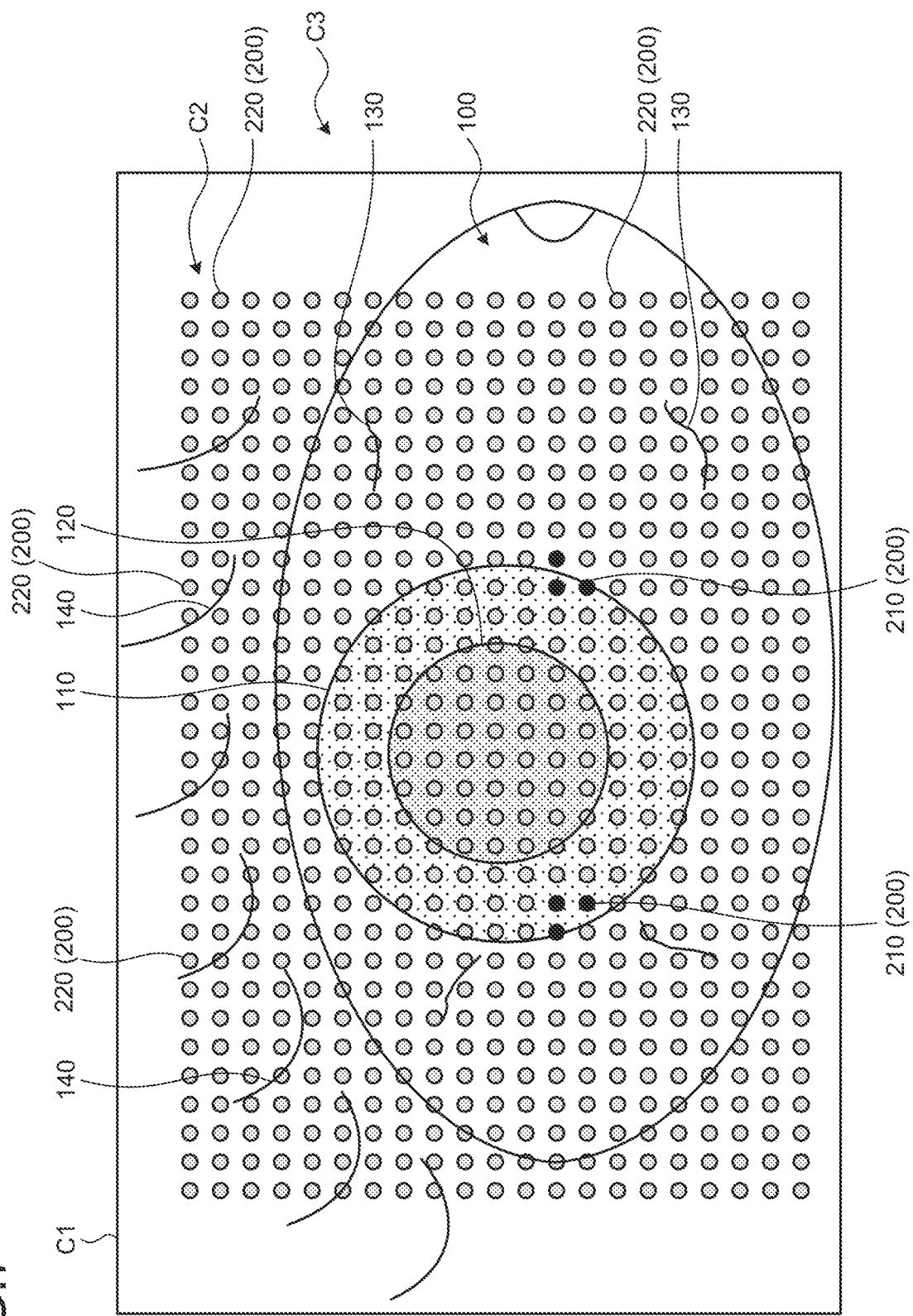
FIG. 7 is a diagram illustrating a superimposed image.

Since the partial first images 210 are selected as described above, as illustrated in FIGS. 6 and 7 for example, even if the center position of the subject eye 100 (the center position of the pupil 120) moves, the partial first images 210 at the position after the movement of the subject eye 100 are selected from among all the first images 200.

The first embodiment described above achieves the following effects.

The control device 5 according to the first embodiment generates the superimposed image C3 in which the pattern image C2 described above and the captured image C1 generated in the surgical microscope 2 are superimposed on each other. Therefore, during surgery, the surgeon may easily determine how much the hand holding the surgical tool moves from the position of each of the first images 200 in the pattern image C2 included in the superimposed image C3 displayed in the display device 3 to move the surgical tool in the superimposed image C3.

Thus, the control device 5 according to the first embodiment makes it possible to easily compare the amount of motion of the hand holding the surgical tool with the amount of movement of the surgical tool in the superimposed image C3, which thereby improves convenience.

In particular, the control device 5 according to the first embodiment extracts an area having a specific feature from the captured image C1, uses, as the partial first images 210, the first images 200 located at a position corresponding to the area in the pattern image C2, and generates the pattern image C2 in which the partial first images 210 may be distinguished from the other first images 220.

Therefore, the surgeon may recognize an area serving as a specific indicator for the cataract surgery (for example, an area indicating the position of a port to be incised in the port creation step) from the position of the partial first images 210 displayed in the display device 3. This further improves the convenience.

In addition, the control device 5 according to the first embodiment generates the pattern image C2 in which the partial first images 210 may be distinguished from the other first images 220 by changing at least one of the brightness and color of the partial first images 210 and transmittance to the captured image C1.

This enables creation of the pattern image C2 that is easy for the surgeon to recognize the partial first images 210 with simple processing.

Second Embodiment

The description goes on to the second embodiment.

In the following description, configurations that are the same as those of the first embodiment are given the same reference signs, and the detailed description thereof is omitted or simplified.

Figure 8:
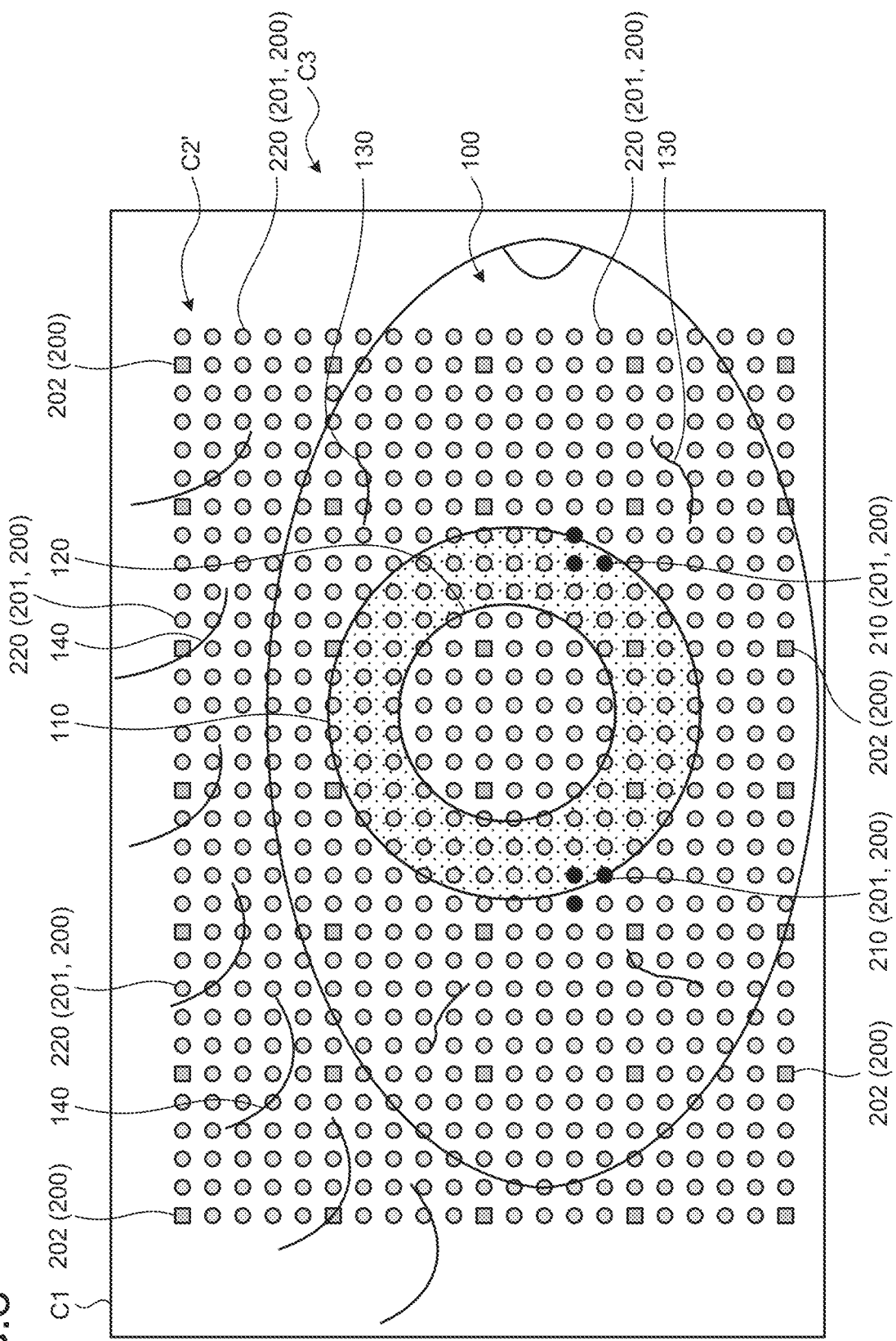
FIG. 8 is a diagram illustrating a superimposed image according to a second embodiment.

FIG. 8 is a diagram illustrating a superimposed image C3 according to the second embodiment. For convenience of explanation, FIG. 8 is a diagram corresponding to FIG. 6.

In the second embodiment, as illustrated in FIG. 8, a pattern image C2 is different from that of the first embodiment. Hereinafter, for convenience of explanation, the pattern image C2 according to the second embodiment is referred to as a pattern image C2'.

As illustrated in FIG. 8, the first images 200 constituting the pattern image C2' include two types of a second image 201 and a third image 202.

The second image 201 is the same image as the first image 200 described in the first embodiment, and is a circular dot.

The third image 202 is an image different from the second image 201. In the second embodiment, the third image 202 is a square dot as illustrated in FIG. 8.

The pattern image C2' is an image in which the first images 200 located at specific positions are replaced with the third images 202 in the pattern image C2 described above. More specifically, the plurality of third images 202 are regularly arranged vertically and horizontally so that four of the second images 201 are sandwiched vertically and horizontally between the third images 202. The number of second images 201 sandwiched by the third images 202 is not limited to four, and may be other numbers.

The second embodiment described above achieves the effects similar to those of the first embodiment and further achieves the following effects.

In the second embodiment, the first images 200 constituting the pattern image C2' include two types of the second and third images 201 and 202.

Therefore, the surgeon may compare, in more detail, the amount of motion of the hand holding the surgical tool with the amount of movement of the surgical tool in the superimposed image C3 on the basis of the position of the second images 201 with a narrow interval and the position of the third image 202 with a wide interval in the first images 200 displayed in the display device 3. In short, the convenience may be further improved.

Third Embodiment

The description goes on to the third embodiment.

In the following description, configurations that are the same as those of the first embodiment are given the same reference signs, and the detailed description thereof is omitted or simplified.

Figure 9:
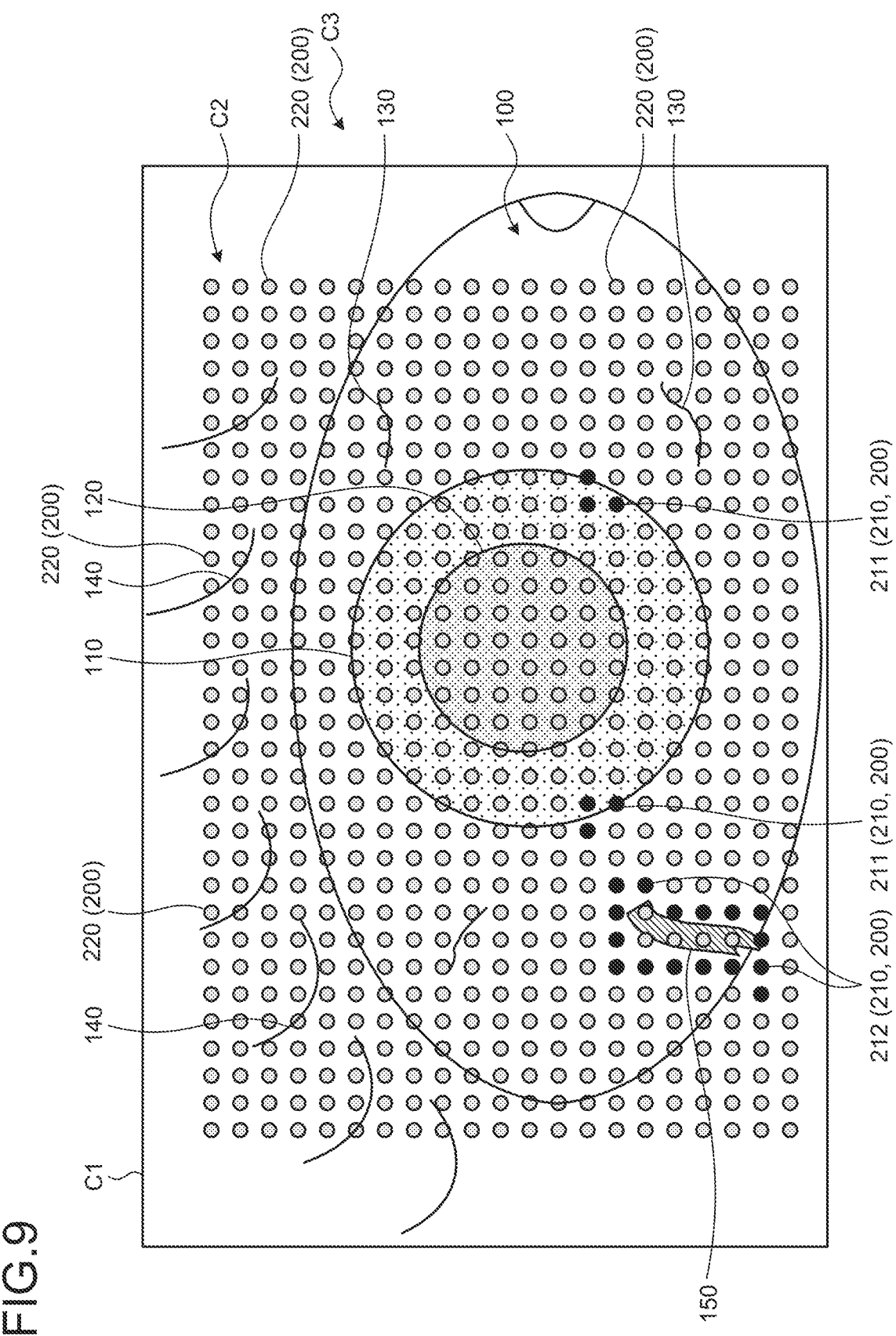
FIG. 9 is a diagram illustrating a superimposed image according to a third embodiment.

FIG. 9 is a diagram illustrating a superimposed image C3 according to the third embodiment. For convenience of explanation, FIG. 9 is a diagram corresponding to FIG. 6. In FIG. 9, an area denoted by the reference sign "150" (hatched area) indicates blood bleeding from the subject eye 100.

The control unit 53 (pattern image controller) according to the third embodiment selects the partial first images 210 from among all the first images 200 in the pattern image C2 in the same manner as in the first embodiment, and also selects the images described below as the partial first images 210. Note that, in the following description, for convenience of explanation, the partial first images 210 selected by using the method described in the first embodiment are referred to as partial first images 211 (FIG. 9), and the partial first images 210 selected by using the method of the third embodiment are referred to as partial first images 212 (FIG. 9).

The control unit 53 (pattern image controller) uses a known method such as image recognition using artificial intelligence (AI) to extract an area having a specific feature (for example, an area where the blood 150, or a staining agent or a fluorescent agent used in surgery is present) from the captured image C1. The control unit 53 (pattern image controller) then uses, as the partial first images 212, the first images 200 located at a position corresponding to the extracted area in the pattern image C2 (for example, a position surrounding the extracted area). In FIG. 9, the partial first images 211 and the partial first images 212 have the same appearance; however, the present invention is not limited thereto, and the partial first images 211 and the partial first images 212 may have different appearances.

The third embodiment described above achieves the effects similar to those of the first embodiment and further achieves the following effects.

The control device 5 according to the third embodiment selects, as the partial first images 210, the partial first images 212 from among all the first images 200 in the pattern image C2 as described above.

Therefore, the surgeon may recognize the area of the bleeding blood 150 or the area where the staining agent or the fluorescent agent used in surgery is present on the basis of the positions of the partial first images 212 displayed in the display device 3. In short, the convenience may be further improved.

Fourth Embodiment

The description goes on to the fourth embodiment.

In the following description, configurations that are the same as those of the third embodiment are given the same reference signs, and the detailed description thereof is omitted or simplified.

Figure 10:
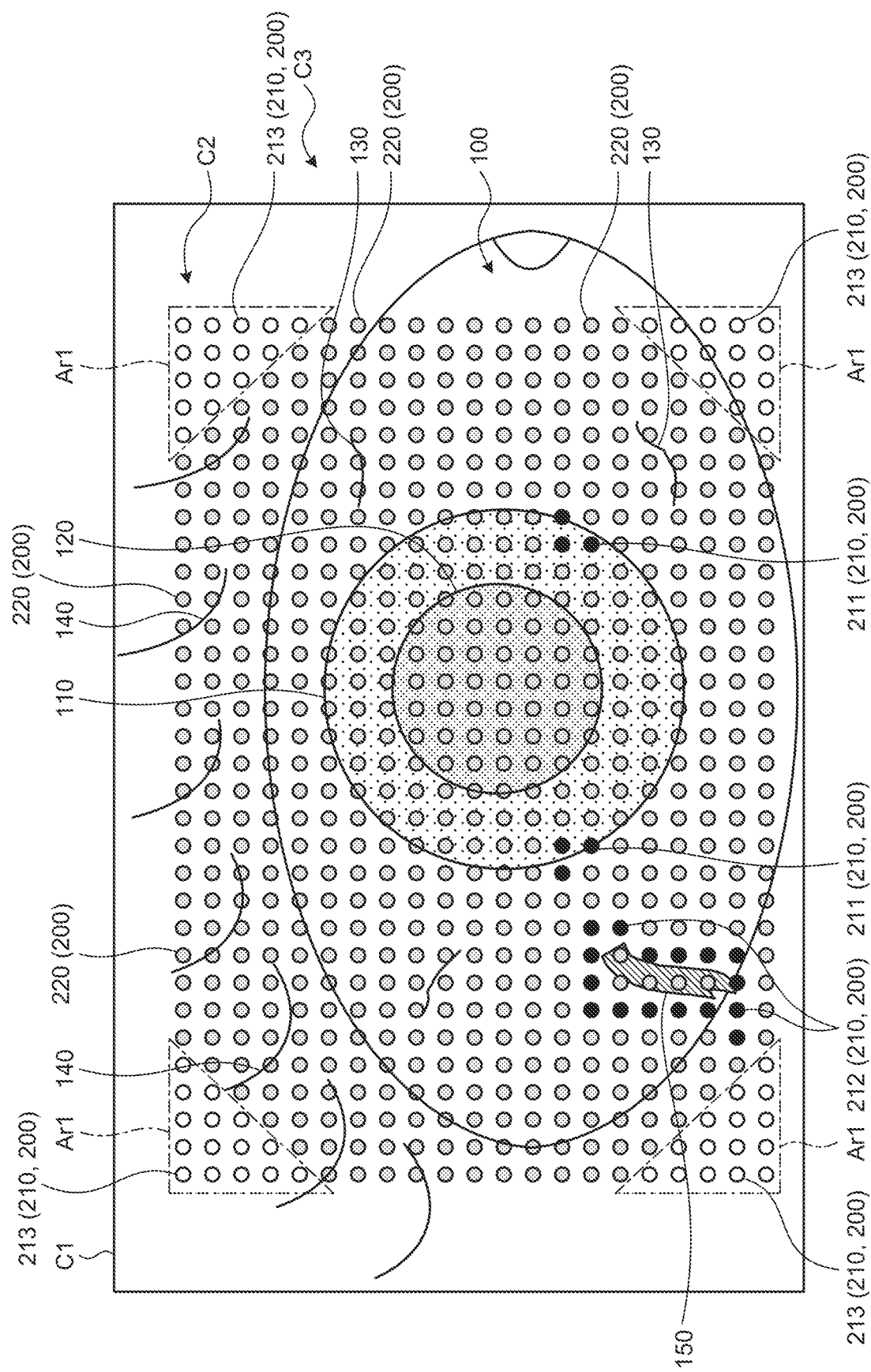
FIG. 10 is a diagram illustrating a superimposed image according to a fourth embodiment.

FIG. 10 is a diagram illustrating a superimposed image C3 according to the fourth embodiment. For convenience of explanation, FIG. 10 is a diagram corresponding to FIG. 6.

The control unit 53 (pattern image controller) according to the fourth embodiment selects the partial first images 210 from among all the first images 200 in the pattern image C2 in the same manner as in the third embodiment, and also selects the images described below as the partial first images 210. Hereinafter, for convenience of explanation, the partial first images 210 selected by using the method of the fourth embodiment are referred to as partial first images 213 (FIG. 10).

The control unit 53 (pattern image controller) uses, as the partial first images 213, the first images 200 located at a position (in the area Ar1, for example) corresponding to a preset area Ar1 (four corner areas in the example of FIG. 10) in the pattern image C2. The control unit 53 (pattern image controller) then performs control to generate a pattern image C2 in which the shape (circular shape) of all the first images 200 remains unchanged and an overall appearance of the partial first images 213 is made less visible with respect to the other first images 200. Examples of the method for making the first images 213 less visible include making the brightness of the partial first images 213 the same as the brightness or color of the captured image C1 at a pixel position around the first images 213, or making the transmittance of the first images 213 with respect to the captured image C1 very high.

The fourth embodiment described above achieves the effects similar to those of the third embodiment and further achieves the following effects.

The control device 5 according to the fourth embodiment selects, as the partial first images 210, the partial first images 213 from among all the first images 200 in the pattern image C2 as described above. The control device 5 then generates a pattern image C2 in which the shape (circular shape) of all the first images 200 remains unchanged and an overall appearance of the partial first images 213 is made less visible with respect to the other first images 200.

This leads to obtain a pattern image C2 in which the partial first images 213 located in unnecessary areas Ar1 such as four corner areas are made less visible and the first images 210 are visible only in a necessary area, which in turn makes the superimposed image C3 displayed in the display device 3 a visible image.

Fifth Embodiment

The description goes on to the fifth embodiment.

In the following description, configurations that are the same as those of the first embodiment are given the same reference signs, and the detailed description thereof is omitted or simplified.

Figure 11:
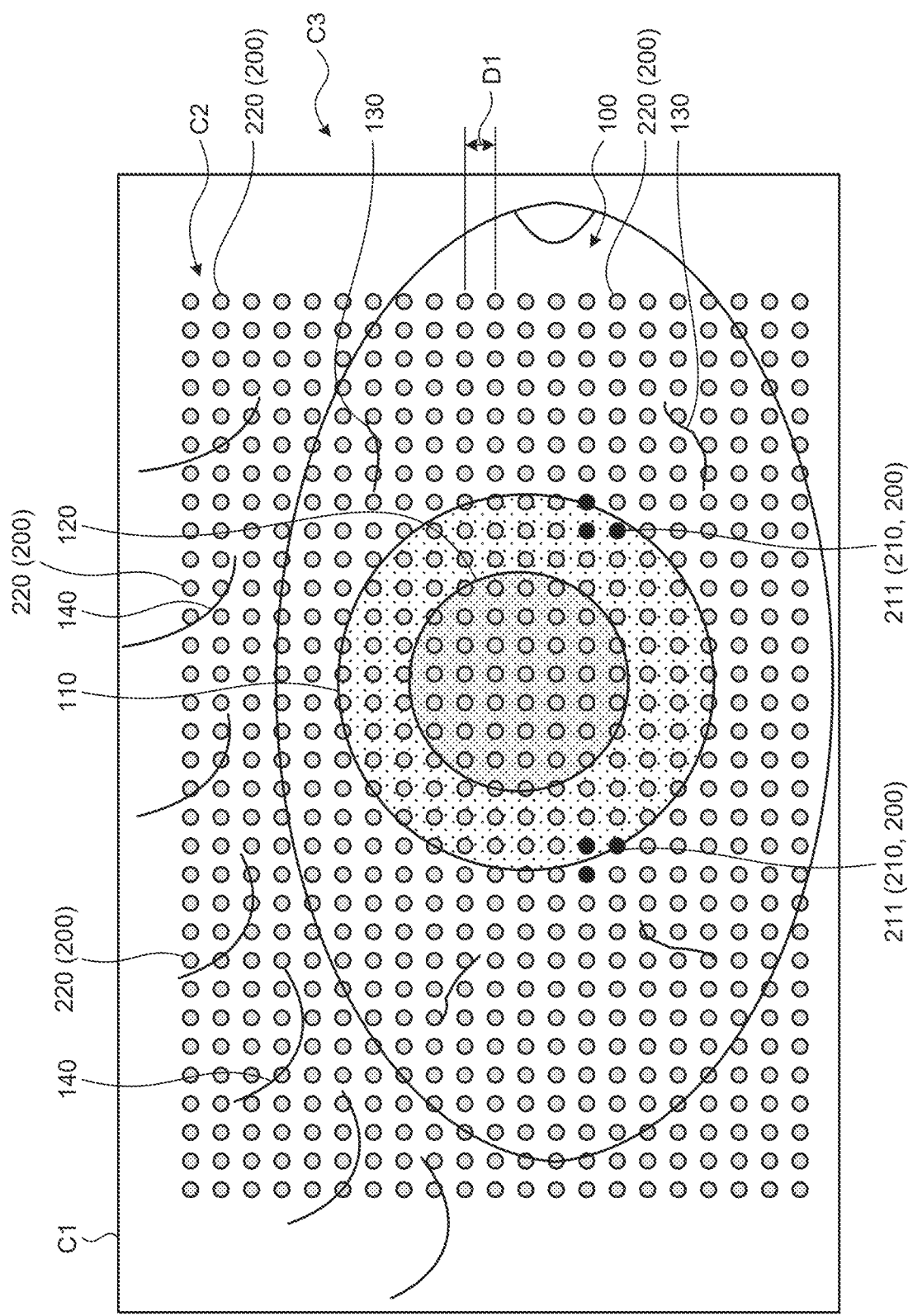
FIG. 11 is a diagram illustrating a superimposed image according to a fifth embodiment.
Figure 12:
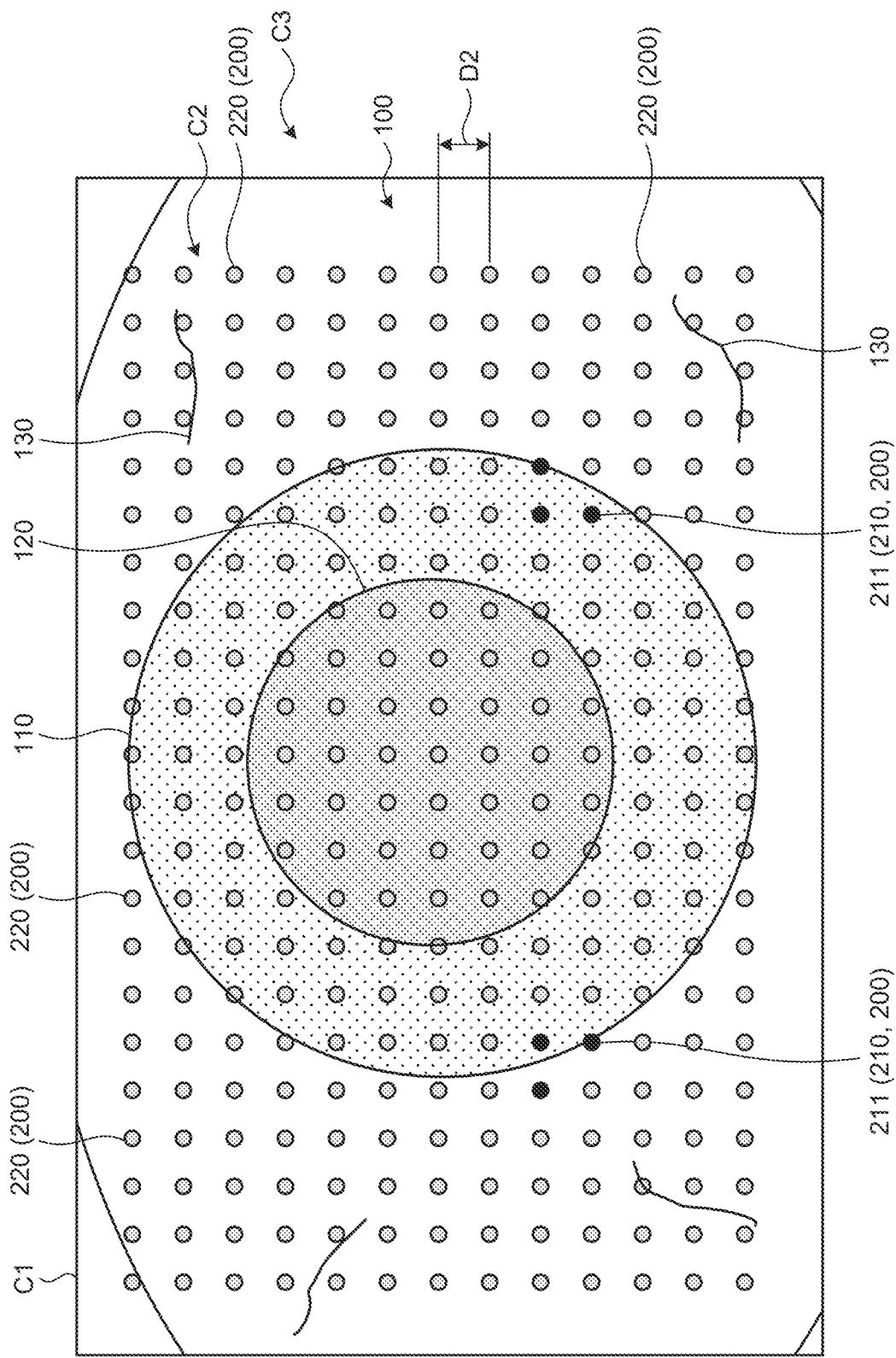
FIG. 12 is a diagram illustrating a superimposed image according to the fifth embodiment.

FIGS. 11 and 12 are diagrams illustrating a superimposed image C3 according to the fifth embodiment. For convenience of explanation, FIGS. 11 and 12 are diagrams corresponding to FIG. 6.

The control unit 53 (pattern image controller) according to the fifth embodiment has the following functions, in addition to the functions described in the first embodiment.

The control unit 53 (pattern image controller) controls the operation of the image processing unit 52 (pattern image generation unit) to change the specific intervals between the first images 200 in the pattern image C2. In the fifth embodiment, the control unit 53 (pattern image controller) changes the specific intervals on the basis of the state of the surgical microscope 2. Specifically, for example, in a case where zoom magnification (zoom magnification of the zooming lens 2214 or zoom magnification in the enlargement processing (electronic zoom) of the image processing unit 52) is lower than a specific magnification threshold, or alternatively, in a case where a subject distance is longer than a specific distance threshold, the control unit 53 (pattern image controller) sets the specific interval at a first interval D1 as illustrated in FIG. 11. On the other hand, in a case where the zoom magnification is higher than the specific magnification threshold, or alternatively, in a case where the subject distance is shorter than the specific distance threshold, the control unit 53 (pattern image controller) sets the specific interval at a second interval D2 larger than the first interval D1 as illustrated in FIG. 12. Here, the subject distance means a distance between the objective lens 2211 and the subject eye, and the subject distance is estimated from, for example, a position (focus position) on the optical axis Ax in the focusing lens 2215.

Note that, according to the method for selecting the partial first images 210 described in the first embodiment, as illustrated in FIGS. 11 and 12, even in a case where the zoom magnification or the subject distance changes, the first image 200 at the post-change position is selected from among all the partial first images 211.

The fifth embodiment described above achieves the effects similar to those of the first embodiment and further achieves the following effects.

The control device 5 according to the fifth embodiment changes the specific intervals between the first images 200 in the pattern image C2 on the basis of the state of the surgical microscope 2.

Therefore, even in a case where the zoom magnification or the subject distance changes, the surgeon may easily compare the amount of motion of the hand holding the surgical tool with the amount of movement of the surgical tool in the superimposed image C3 on the basis of the position of the first image 200 displayed in the display device 3.

Sixth Embodiment

The description goes on to the sixth embodiment.

In the following description, configurations that are the same as those of the first embodiment are given the same reference signs, and the detailed description thereof is omitted or simplified.

Figure 13:
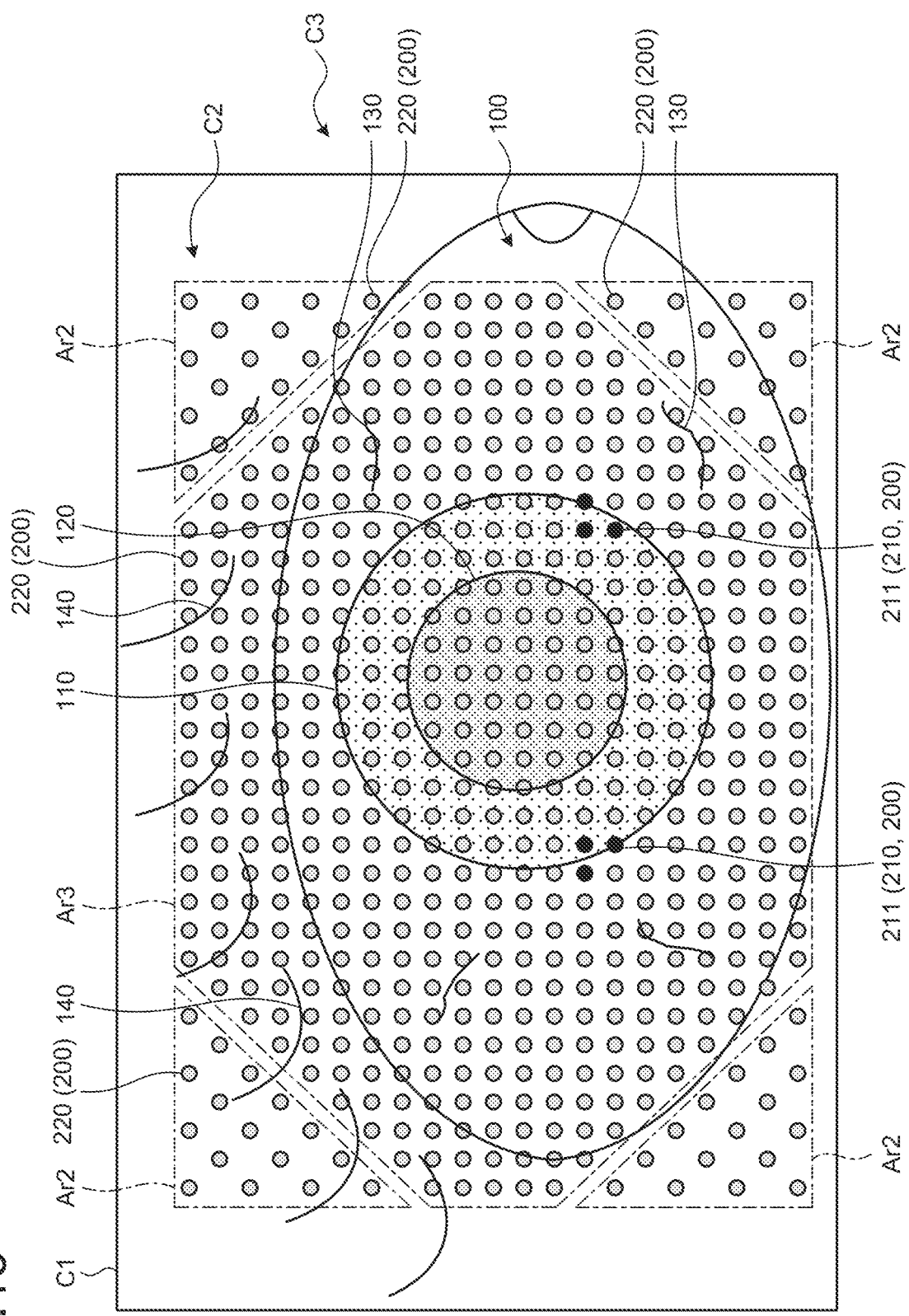
FIG. 13 is a diagram illustrating a superimposed image according to a sixth embodiment.

FIG. 13 is a diagram illustrating a superimposed image C3 according to the sixth embodiment. For convenience of explanation, FIG. 13 is a diagram corresponding to FIG. 6.

The control unit 53 (pattern image controller) according to the sixth embodiment has the following functions, in addition to the functions described in the first embodiment.

The control unit 53 (pattern image controller) controls the operation of the image processing unit 52 (pattern image generation unit) to change the specific intervals between the first images 200 in the pattern image C2. In the sixth embodiment, as illustrated in FIG. 13, the control unit 53 (pattern image controller) makes the interval between the first images 200 located in a first area Ar2 (four corner areas in the example of FIG. 13) in the pattern image C2 different from the interval between the first images 200 located in a second area Ar3 other than the first area Ar2 in the pattern image C2. Specifically, the control unit 53 increases the distance between the first images 200 located in the first area Ar2 and reduces the distance between the first images 200 located in the second area Ar3.

The sixth embodiment described above achieves the effects similar to those of the first embodiment and further achieves the following effects.

The control device 5 according to the sixth embodiment makes the interval between the first images 200 located in the first area Ar2 in the pattern image C2 different from the interval between the first images 200 located in the second area Ar3 in the pattern image C2.

This leads to obtain a pattern image C2 in which the first images 200 located in unnecessary areas (first areas Ar2) such as four corner areas are made less visible and the first images 200 are visible only in a necessary area (second area Ar3), which in turn makes the superimposed image C3 displayed in the display device 3 a visible image.

Seventh Embodiment

The description goes on to the seventh embodiment.

In the following description, configurations that are the same as those of the first embodiment are given the same reference signs, and the detailed description thereof is omitted or simplified.

Figure 14:
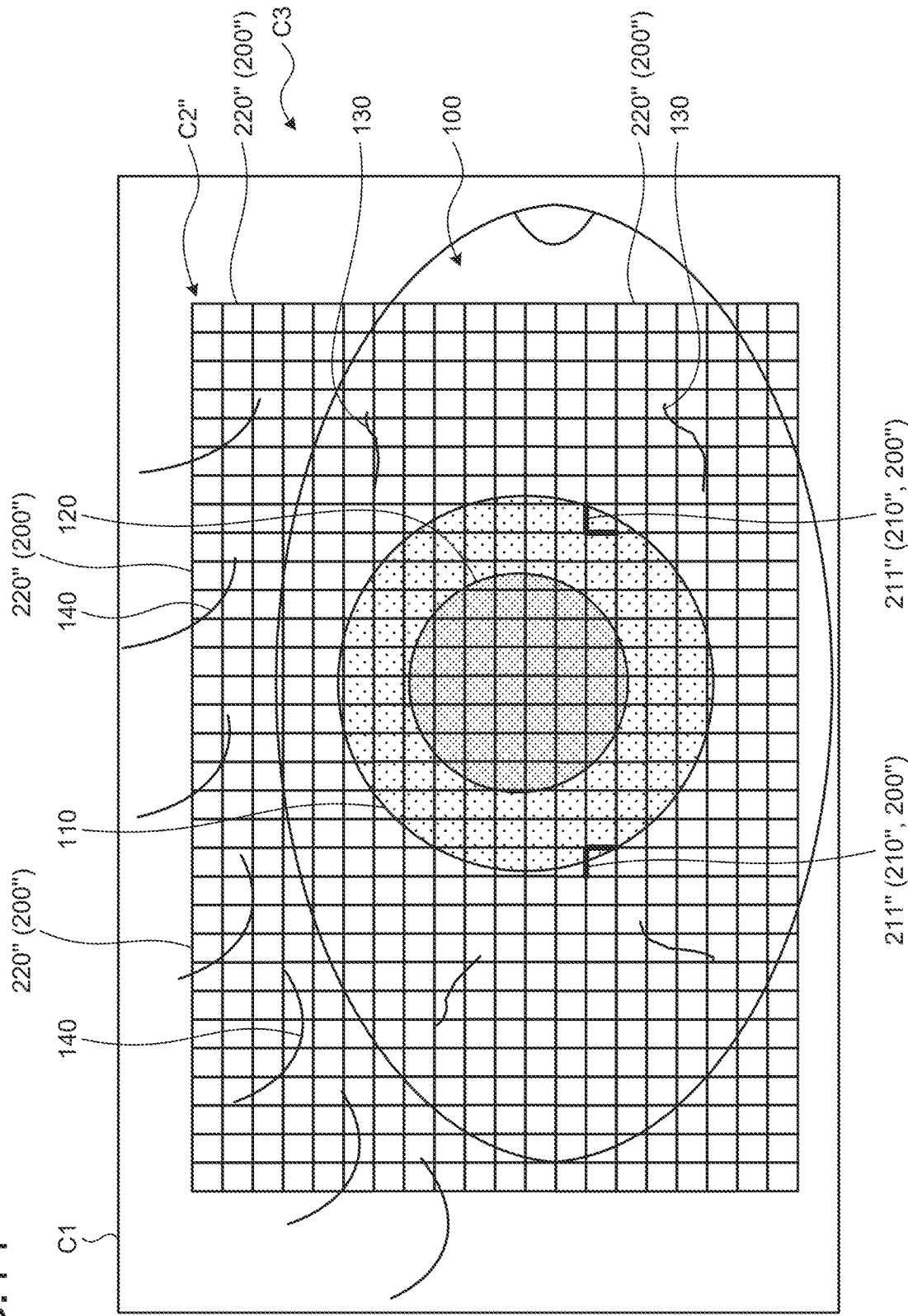
FIG. 14 is a diagram illustrating a superimposed image according to a seventh embodiment.

FIG. 14 is a diagram illustrating a superimposed image C3 according to the seventh embodiment. For convenience of explanation, FIG. 14 is a diagram corresponding to FIG. 6.

In the seventh embodiment, as illustrated in FIG. 14, the pattern image C2 is different from that of the first embodiment. Hereinafter, for convenience of explanation, the pattern image C2 according to the seventh embodiment is referred to as a pattern image C2″. Further, the first image 200 according to the seventh embodiment is referred to as a first image 200″. Further, the partial first images 210, 211 according to the seventh embodiment are referred to as partial first images 210″, 211″. In addition, other first images 220 according to the seventh embodiment are referred to as the other first images 220″.

The first image 200″ has a square frame shape as illustrated in FIG. 14. The pattern image C2″ is a mesh-like (lattice-like) image in which a plurality of first images 200″ is arranged in parallel in a specific pattern (in the example of FIG. 14, arranged in parallel to be in contact with one another vertically and horizontally).

The control unit 53 (pattern image controller) according to the seventh embodiment performs control to generate a pattern image C2″ in which the partial first images 210″, 211″ may be distinguished from the other first images 220″ by changing the appearance of a part of the entirety of the partial first images 210″, 211″ (only two adjacent sides of the frame shape in the example of FIG. 14) without changing the shape (frame shape) of each of the first images 200″. The method for changing the appearance is similar to the method described in the first embodiment (method for changing at least one of the brightness, the color, and the transmittance to the captured image C1). In FIG. 14, for convenience of explanation, the changed part is represented by a thick black line, and the other parts are represented by a thin black line.

Even in the case of applying the pattern image C2″ as in the seventh embodiment, the effects similar to those of the first embodiment are achieved.

Eighth Embodiment

The description goes on to the eighth embodiment.

In the following description, configurations that are the same as those of the first embodiment are given the same reference signs, and the detailed description thereof is omitted or simplified.

Figure 15:
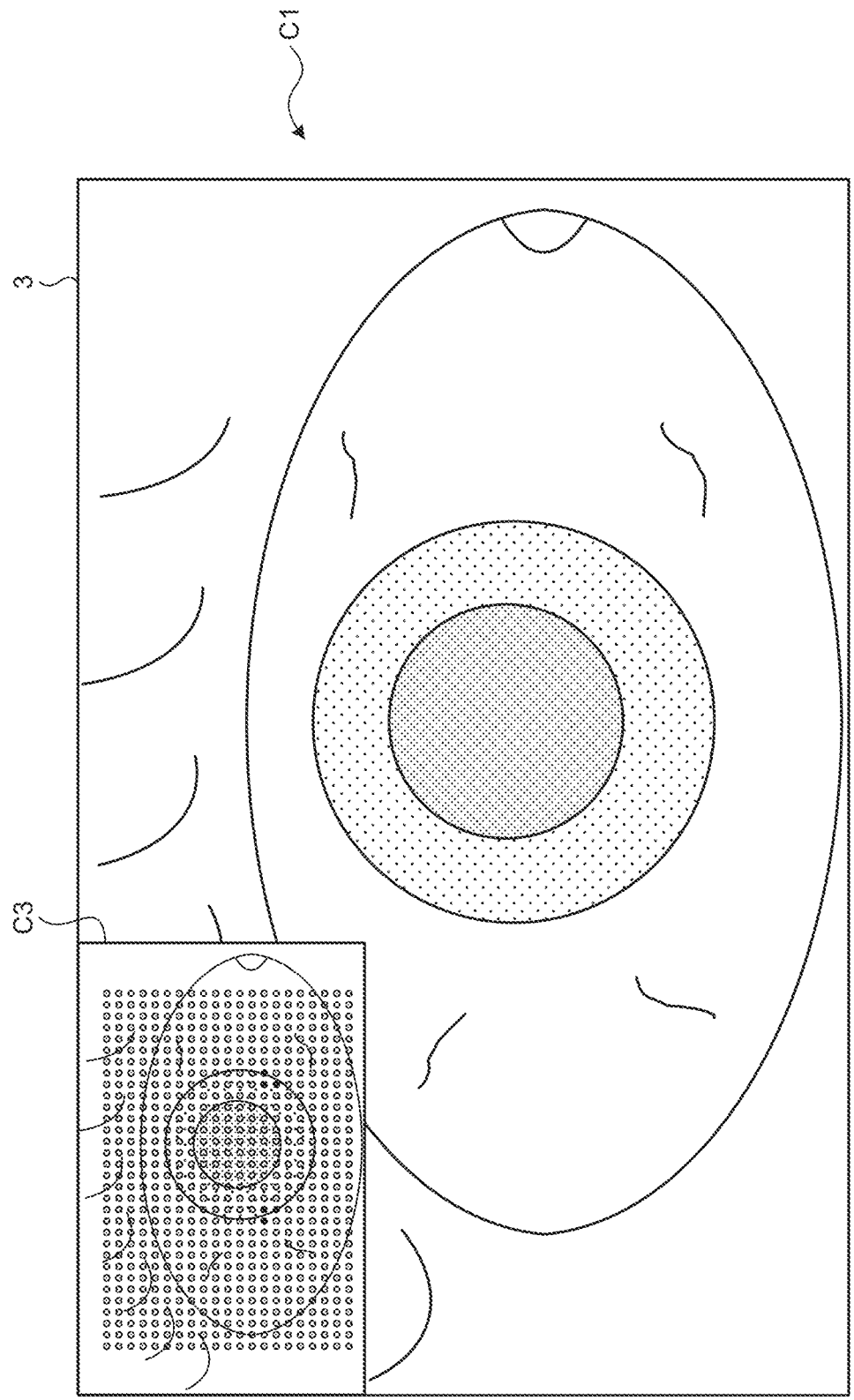
FIG. 15 is a diagram illustrating a display format of a superimposed image according to an eighth embodiment.

FIG. 15 is a diagram illustrating a display format of a superimposed image C3 according to the eighth embodiment. In FIG. 15, the captured image C1 is the same as the captured image C1 illustrated in FIG. 3, and the superimposed image C3 is the same as the superimposed image C3 illustrated in FIG. 6.

The image processing unit 52 (display controller) according to the first embodiment uses the superimposed image C3 as an image for display, and displays only the superimposed image C3 in the display device 3.

On the other hand, the image processing unit 52 (display controller) according to the eighth embodiment uses the captured image C1 and the superimposed image C3 as images for display. The image processing unit 52 (display controller) generates a video signal for display with which to display the images for display (captured image C1 and superimposed image C3) in the display device 3, and outputs the video signal to the display device 3. In the eighth embodiment, the image processing unit 52 (display controller) generates a video signal for display with which to display the captured image C1 as a master image and the superimposed image C3 as a slave image in the picture-in-picture format, and outputs the video signal to the display device 3. Consequently, as illustrated in FIG. 15, the captured image C1 (master image) and the superimposed image C3 (slave image) are displayed in the picture-in-picture (PinP) format in the display device 3.

The eighth embodiment described above achieves the effects similar to those of the first embodiment and further achieves the following effects.

The control device 5 according to the eighth embodiment uses the captured image C1 and the superimposed image C3 as images for display.

This allows the surgeon to visually recognize the captured image C1 and the superimposed image C3 separately in the display device 3, which enables the surgeon to perform the surgery more smoothly.

Ninth Embodiment

The description goes on to the ninth embodiment.

In the following description, configurations that are the same as those of the first embodiment are given the same reference signs, and the detailed description thereof is omitted or simplified.

Figure 16:
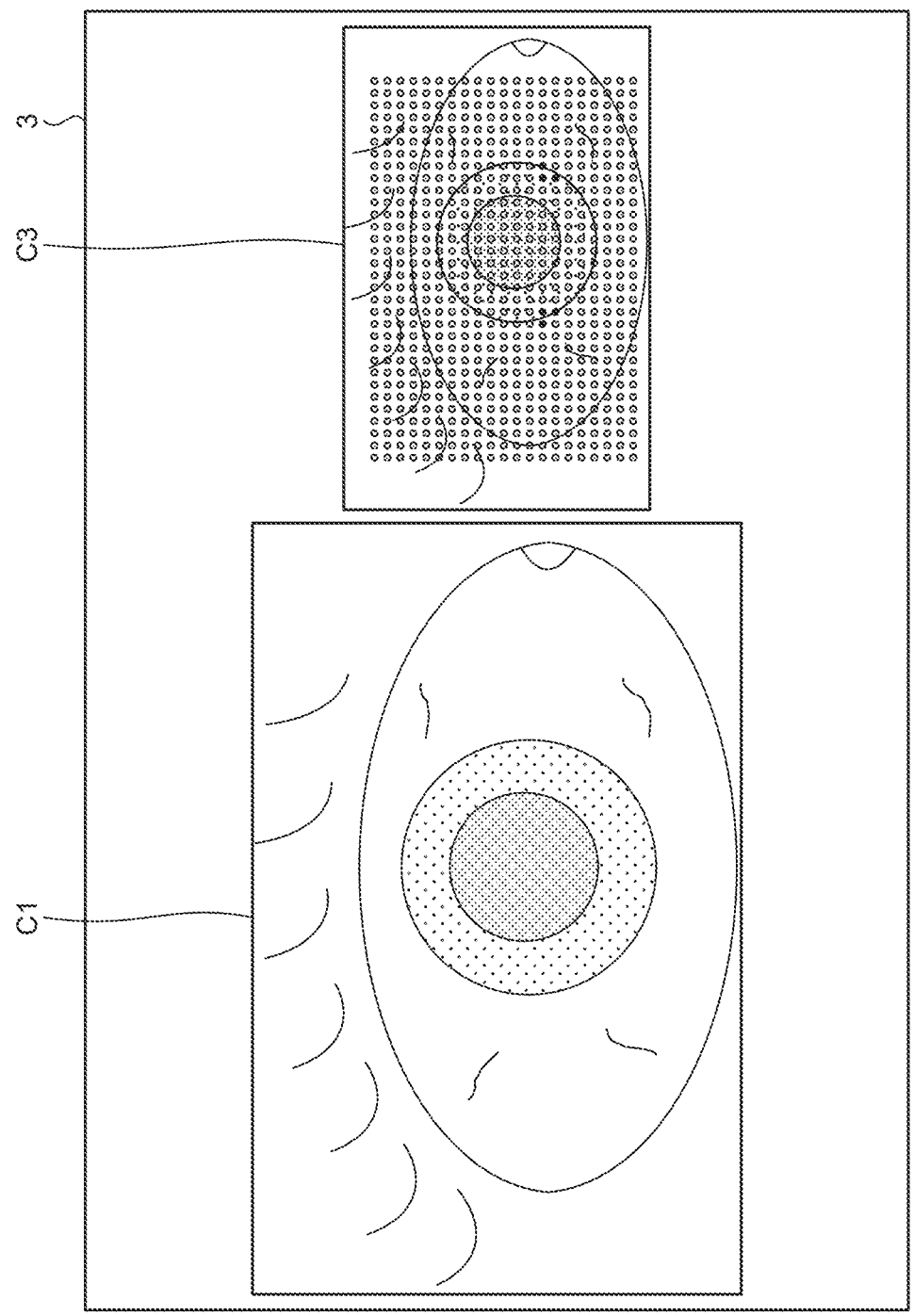
FIG. 16 is a diagram illustrating a display format of a superimposed image according to a ninth embodiment.

FIG. 16 is a diagram illustrating a display format of the superimposed image C3 according to the ninth embodiment. In FIG. 16, the captured image C1 is the same as the captured image C1 illustrated in FIG. 3, and the superimposed image C3 is the same as the superimposed image C3 illustrated in FIG. 6.

The image processing unit 52 (display controller) according to the first embodiment uses the superimposed image C3 as an image for display, and displays only the superimposed image C3 in the display device 3.

On the other hand, the image processing unit 52 (display controller) according to the ninth embodiment uses the captured image C1 and the superimposed image C3 as images for display. The image processing unit 52 (display controller) generates a video signal for display with which to display the images for display (captured image C1 and superimposed image C3) in the display device 3, and outputs the video signal to the display device 3. In the ninth embodiment, the image processing unit 52 (display controller) generates a video signal for display with which to display the captured image C1 and the superimposed image C3 in the picture-out-picture (PoP) format, and outputs the video signal to the display device 3. Consequently, as illustrated in FIG. 16, the captured image C1 and the superimposed image C3 are displayed side by side in the picture-out-picture format in the display device 3.

Even in the case of applying the display format such as that in the ninth embodiment, the effects similar to those of the first and eighth embodiments are achieved.

Tenth Embodiment

The description goes on to the tenth embodiment.

In the following description, configurations that are the same as those of the first embodiment are given the same reference signs, and the detailed description thereof is omitted or simplified.

Figure 17:
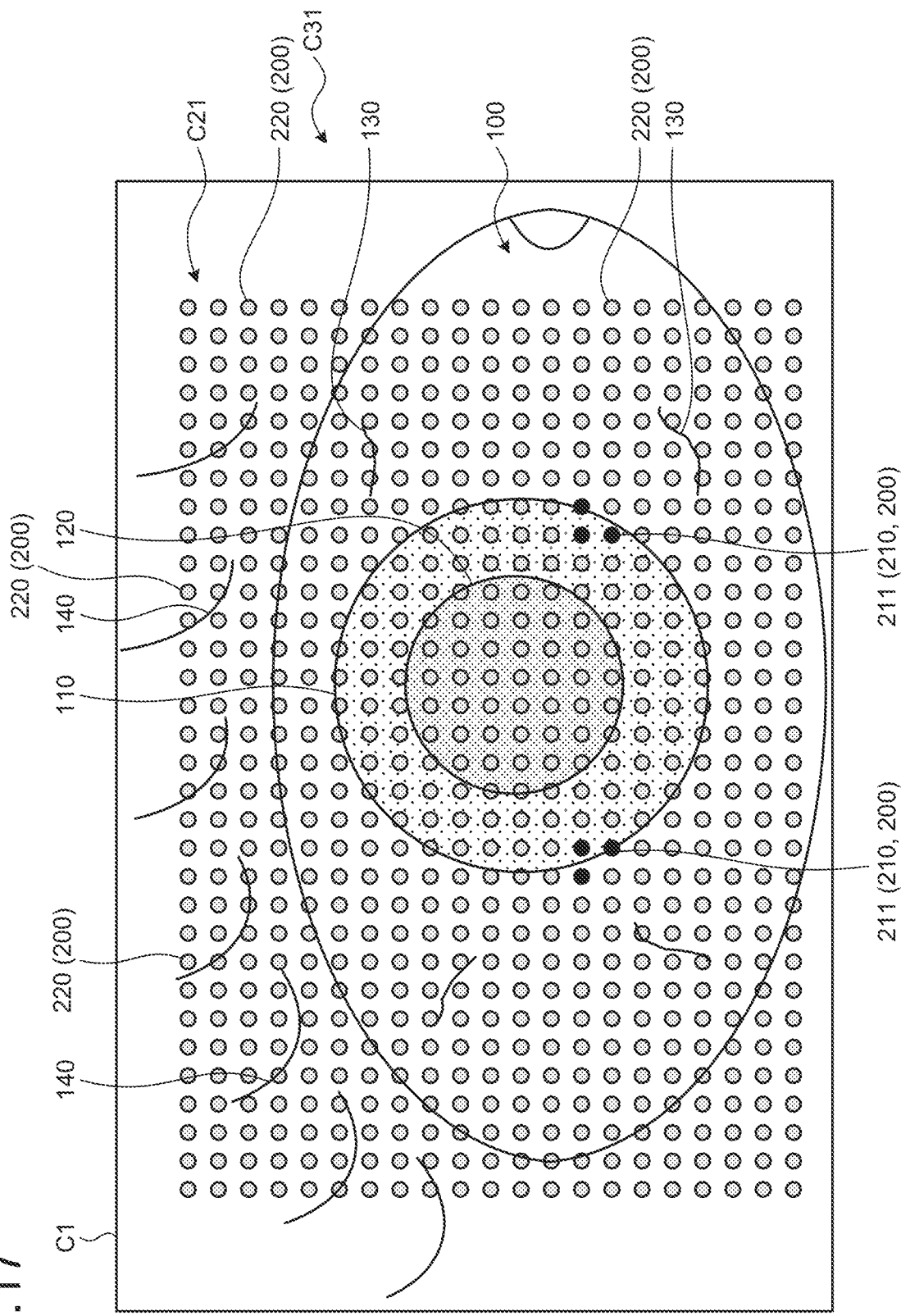
FIG. 17 is a diagram illustrating a first superimposed image according to a tenth embodiment.
Figure 18:
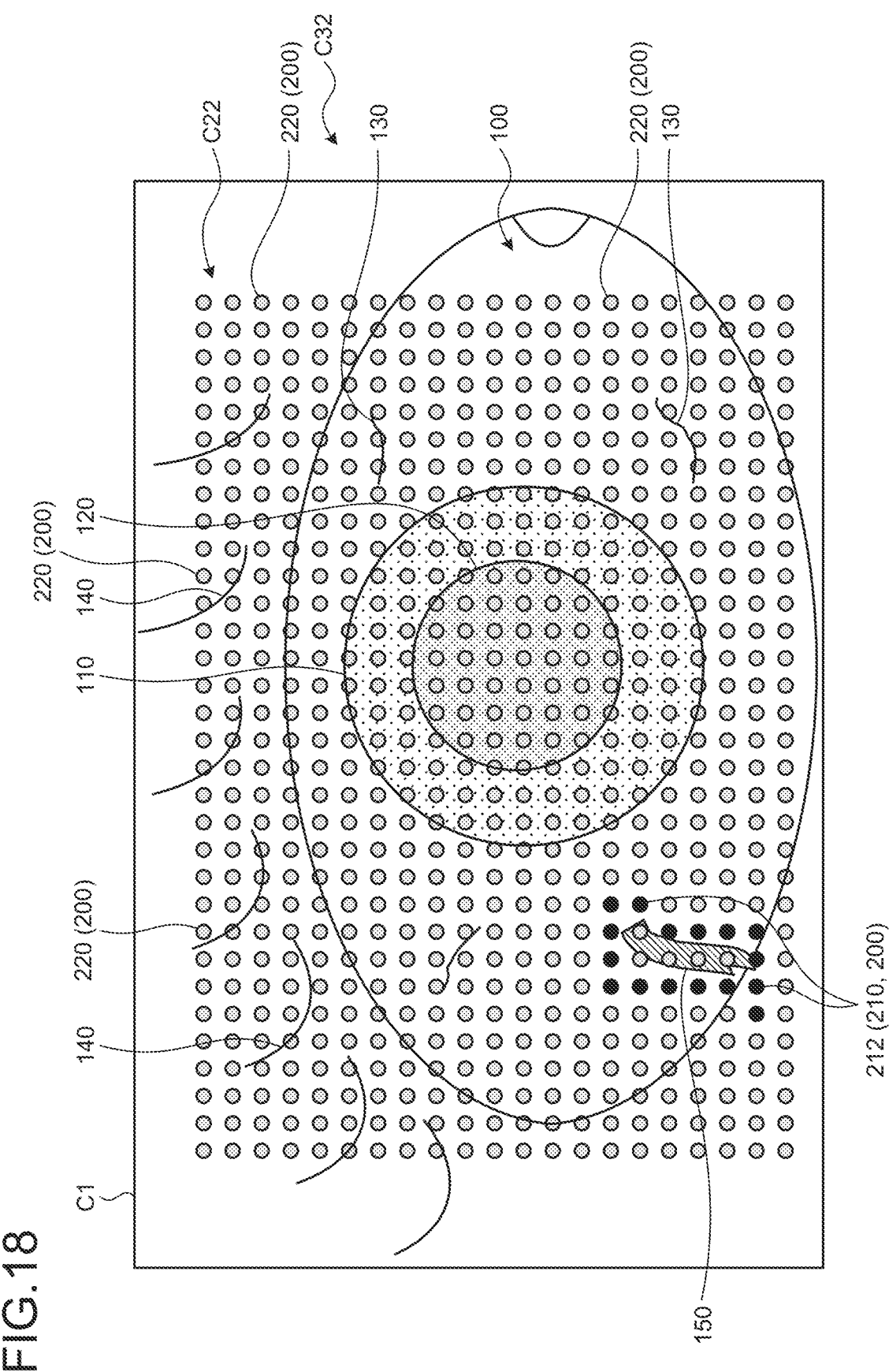
FIG. 18 is a diagram illustrating a second superimposed image according to the tenth embodiment.
Figure 19:
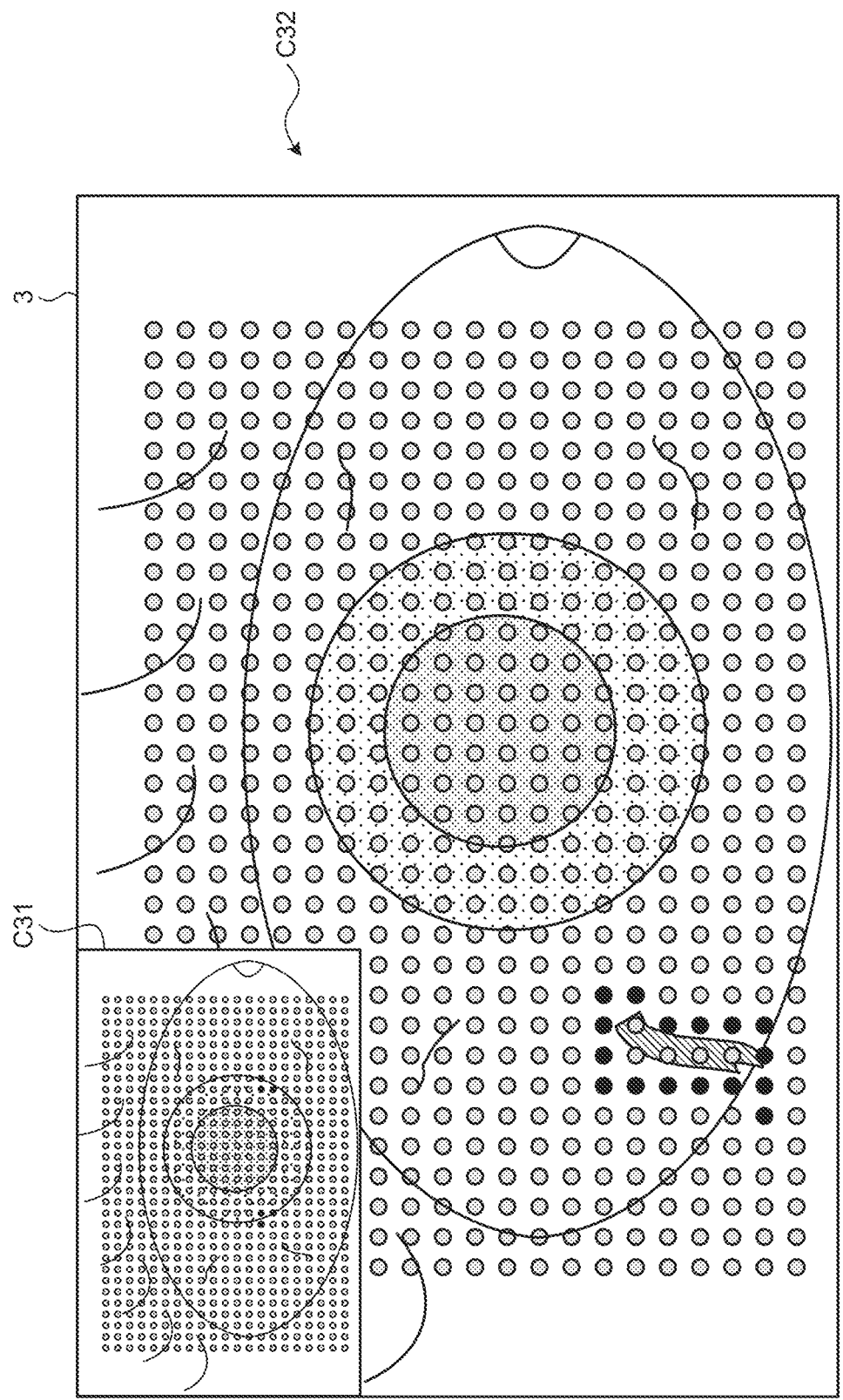
FIG. 19 is a diagram illustrating a display format of the first and second superimposed images according to the tenth embodiment.

FIG. 17 is a diagram illustrating a first superimposed image C31 according to the tenth embodiment. FIG. 18 is a diagram illustrating a second superimposed image C32 according to the tenth embodiment. FIG. 19 is a diagram illustrating a display format of the first and second superimposed images C31 and C32 according to the tenth embodiment. For convenience of explanation, FIGS. 17 and 18 are diagrams corresponding to FIG. 6. In FIG. 19, the first superimposed image C31 is the same as the first superimposed image C31 illustrated in FIG. 17, and the second superimposed image C32 is the same as the second superimposed image C32 illustrated in FIG. 18.

The image processing unit 52 (display controller) according to the first embodiment uses the superimposed image C3 as an image for display, and displays only the superimposed image C3 in the display device 3.

On the other hand, in the tenth embodiment, the display format of the image in the display device 3 by the control device 5 is different.

In the control device 5 according to the tenth embodiment, the image processing unit 52 (pattern image generation unit) generates two pattern images C2 under the control of the control unit 53 (pattern image controller). Hereinafter, for convenience of explanation, one of the two pattern images C2 is referred to as a first pattern image C21 (FIG. 17), and the other pattern image is referred to as a second pattern image C22 (FIG. 18).

The first pattern image C21 is the same as the pattern image C2 illustrated in FIG. 6. In other words, as described in the first embodiment, the control unit 53 (pattern image controller) finds out a positional relationship between corresponding pixels of the preoperative image and the captured image C1 on the basis of at least one of structural features of the subject eye 100 included in the preoperative image and the captured image C1, for example, the contour of the pupil 120, the contour of the cornea 110 (the contour of an iris), the pattern of the iris, and the shape of the blood vessel 130 of the sclera. Further, the control unit 53 (pattern image controller) extracts, from the captured image C1, an area corresponding to the area identified in the preoperative image (area serving as a specific indicator) (extracts an area having a first feature in the captured image C1). The control unit 53 (pattern image controller) then performs control to generate the first pattern image C21 (FIG. 17) in which the first images 200 located at a position corresponding to the extracted area in the pattern image C2 (within the extracted area, for example) are used as the partial first images 211.

The image processing unit 52 (superimposed image generation unit) then generates the first superimposed image C31 (FIG. 17) in which the first pattern image C21 generated as described above and the captured image C1 (FIG. 3) generated by the imaging unit 223 and acquired via the communication unit 51 are superimposed on each other.

The second pattern image C22 is an image generated as described below.

To be specific, as described in the third embodiment, the control unit 53 (pattern image controller) uses a known method such as image recognition using artificial intelligence (AI) to extract an area having a second feature (for example, an area where the blood 150, or a staining agent or a fluorescent agent used in surgery is present) from the captured image C1. The control unit 53 (pattern image controller) then performs control to generate the second pattern image C22 (FIG. 18) in which the first images 200 located at a position corresponding to the extracted area in the pattern image C2 (position surrounding the extracted area, for example) are used as the partial first images 212.

The image processing unit 52 (superimposed image generation unit) then generates the second superimposed image C32 (FIG. 18) in which the second pattern image C22 generated as described above and the captured image C1 (FIG. 3) generated by the imaging unit 223 and acquired via the communication unit 51 are superimposed on each other.

After the above, the image processing unit 52 (display controller) uses the first superimposed image C31 and the second superimposed image C32 as images for display. The image processing unit 52 (display controller) generates a video signal for display with which to display the images for display (first and second superimposed images C31 and C32) in the display device 3, and outputs the video signal to the display device 3. In the tenth embodiment, the image processing unit 52 (display controller) generates a video signal for display with which to display the second superimposed image C32 as a master image and the first superimposed image C31 as a slave image in the picture-in-picture format, and outputs the video signal to display device 3. Consequently, as illustrated in FIG. 19, the first superimposed image C31 (slave image) and the second superimposed image C32 (master image) are displayed in the picture-in-picture format in the display device 3. Note that the first superimposed image C31 may be used as the master image, and the second superimposed image C32 may be used as the slave image. Further, the first and second superimposed images C31 and C32 may be configured to be displayed in the picture-out-picture format as with the ninth embodiment.

The tenth embodiment described above achieves the effects similar to those of the first embodiment and further achieves the following effects.

The control device 5 according to the tenth embodiment uses the first and second superimposed images C31 and C32 as images for display.

This allows the surgeon to visually recognize the first and second superimposed images C31 and C32 separately in the display device 3, which enables the surgeon to perform the surgery more smoothly.

Other Embodiments

Although the embodiments for carrying out the present disclosure have been described so far, the present disclosure should not be limited only to the first through tenth embodiments.

FIGS. 20A to 20F are diagrams illustrating modifications to the first through sixth and the eighth through tenth embodiments.

In the first through sixth and the eighth through tenth embodiments, the overall appearance of the partial first images 210 is changed without changing the shape (circular shape) of all the first images 200; however, the present invention is not limited thereto. For example, as illustrated in FIGS. 20A to 20F, a partial appearance of the partial first images 210 may be changed. In FIGS. 20A to 20F, a part of which the appearance is changed is indicated in black. Note that the method for changing the appearance is similar to the method described in the first embodiment (method for changing at least one of the brightness, the color, and the transmittance to the captured image C1).

FIGS. 21A to 21K are diagrams illustrating modifications to the first through tenth embodiments.

In the first through tenth embodiments, the shape of the first image 200 is not limited to the shapes described in the first through tenth embodiments, and other shapes may be used. For example, as illustrated in FIGS. 21A to 21K, a "*" shape in which three straight lines intersect at the center may be used as the first image 200. In addition, in a case where the shape is used, the overall appearance of the partial first images 210 may be changed as illustrated in FIG. 21A, or a partial appearance of the entirety of partial first images 210 may be changed as illustrated in FIGS. 21B to 21K. In FIGS. 21A to 21K, a part of which the appearance is changed is indicated in black, and the other parts are represented in dots. Note that the method for changing the appearance is similar to the method described in the first embodiment (method for changing at least one of the brightness, the color, and the transmittance to the captured image C1).

Further, as the shape of the first image 200, in addition to the circular shape, the rectangular shape, and the "*" shape, a triangular shape, another polygonal shape, a "+" shape, or the like may be used.

In the first through tenth embodiments, the pattern image C2 (C2', C21, C21) may be an image rotated by a specific angle (45°, for example).

In the fifth embodiment, the control unit 53 (pattern image controller) performs control to change the specific intervals between the first images 200 in the pattern image C2 on the basis of the state of the surgical microscope 2; however, the present invention is not limited thereto. For example, the control unit 53 (pattern image controller) may perform control to change the specific intervals between the first images 200 in the pattern image C2 on the basis of a specific feature portion in the subject eye (subject) included in the captured image C1. Here, the pupil 120 and the like may be exemplified as the specific feature portion. To be specific, the control unit 53 (pattern image controller) may perform control so that the specific interval is set at 1/n of the diameter of the pupil 120.

According to such a configuration, even in a case where the size of the subject eye displayed in the display device 3 changes, the surgeon may easily compare the amount of motion of the hand holding the surgical tool with the amount of movement of the surgical tool in the superimposed image C3 on the basis of the position of the first image 200 displayed in the display device 3. In short, the convenience may be further improved.

In such a case, the display range of the pattern image C2 may indicate a range in which the specific feature portion may be detected. This allows the surgeon to detect the specific feature portion by operating the surgical microscope 2 so that the specific feature portion falls within the display range of the pattern image C2.

In the first through tenth embodiments, in order to change the appearance of the partial first images 210, the appearance may be changed in association with the brightness or color of the captured image C1 at the pixel position around the partial first images 210.

For example, the appearance of the partial first images 210 may be changed to have a color opposite to the color of the captured image C1 at the pixel position around the partial first images 210.

Further, for example, the appearance of the partial first images 210 may be changed to have brightness lower than the brightness of the captured image C1 by a specific ratio (20%, for example) at the pixel position around the partial first images 210.

In the first through tenth embodiments, the dimensions of the interval between the first images 200 in the pattern image C2 may be displayed in the display device 3. The dimensions may be calculated from, for example, image-capturing conditions (focus position, zoom magnification, subject distance, and the like).

In the first through tenth embodiments, the medical observation system 1 may be implemented by a system that displays an image in three dimensions. To be specific, the display device 3 may be configured by an active or passive three-dimensional display, and the microscope unit 22 may have a function as a stereo camera.

In such a case, the pattern image C2 (C2', C21, C21) may be displayed as a three-dimensional or two-dimensional image.

In a case where the pattern image C2 (C2', C21, C21) is displayed as a two-dimensional image, the pattern image C2 (C2', C21, C21) is incorporated into only one of the left-eye image and the right-eye image, or the identical pattern image C2 (C2', C21, C21) is incorporated into both the images.

Further, in a case where the pattern image C2 (C2', C21, C21) is displayed as a three-dimensional image, at a time when the observation direction by the surgical microscope 2 is oblique, the interval between the first images 200 may be changed as in a bird's eye view. In such a case, a detection function (three-dimensional measurement, arm angle detection, position detection with an external sensor, and the like) of a three-dimensional space may be used to create the pattern image C2 (C2', C21, C21).

In the first through tenth embodiments, the cataract surgery is exemplified as an example of ophthalmic surgery; however, the medical observation system 1 according to the present disclosure is of course applicable to other surgery and the like.

In the first through tenth embodiments, the surgical microscope 2 including the eyepiece 222 is exemplified as the medical observation device according to the present disclosure; however, the present invention is not limited thereto, and a surgical microscope dedicated for heads up surgery (HUS) without the eyepiece 222 may be used.

In the first through tenth embodiments, the variable-focus surgical microscope 2 having the focusing lens 2215 is exemplified as the medical observation device according to the present disclosure; however, the present invention is not limited thereto, and a fixed-focus surgical microscope may be used. In particular, as long as the microscope unit 22 is movable in the Z-direction, the fixed-focus surgical microscope may be used.

In the first through tenth embodiments, the surgical microscope 2 in which the microscope unit 22 is movable in the X-direction, the Y-direction, and the Z-direction is exemplified as the medical observation device according to the present disclosure; however, the present invention is not limited thereto. As the medical observation device according to the present disclosure, for example, a surgical microscope capable of performing XY tilt in which the microscope unit 22 is rotated about an axis along the X-direction and the microscope unit 22 is rotated about an axis along the Y-direction may be used.

Note that the following configurations also falls within the technical scope of the present disclosure.

(1) A medical image processing device including: image acquisition unit configured to acquire image information obtained by imaging with a medical observation device; and superimposed image generation circuitry configured to generate a superimposed image in which a pattern image having first images with a specific shape arranged in parallel in a specific pattern and a captured image based on the image information are superimposed on each other.

(2) The medical image processing device according to (1), further including: a pattern image generation circuitry configured to generate the pattern image; and a pattern image controller configured to control an operation of the pattern image generation circuitry to generate the pattern image in which partial first images of all the first images in the pattern image are distinguishable from the other first images.

(3) The medical image processing device according to (2), wherein the pattern image controller is configured to perform control to generate the pattern image in which the partial first images are distinguishable from the other first images by changing an overall appearance of the partial first images without changing a shape of the partial first images and a shape of the other first images.

(4) The medical image processing device according to (2), wherein the pattern image controller is configured to perform control to generate the pattern image in which the partial first images are distinguishable from the other first images by changing a partial appearance of all of the partial first images without changing a shape of the partial first images and a shape of the other first images.

(5) The medical image processing device according to any one of (2) to (4), wherein the pattern image controller is configured to perform control to generate the pattern image in which the partial first images are distinguishable from the other first images by changing at least one of brightness and color of the partial first images and transmittance to the captured image.

(6) The medical image processing device according to any one of (2) to (5), wherein the pattern image controller is configured to extract an area having a specific feature from the captured image, and uses, as the partial first images, the first images located at a position corresponding to the area in the pattern image.

(7) The medical image processing device according to any one of (2) to (6), wherein the pattern image controller is configured to use, as the partial first images, the first images located at a position corresponding to a preset area in the pattern image.

(8) The medical image processing device according to (7), wherein the pattern image controller is configured to perform control to generate the pattern image in which the partial first images are distinguishable from the other first images by making an overall appearance of the partial first images less visible with respect to the other first images without changing a shape of the partial first images and a shape of the other first images.

(9) The medical image processing device according to any one of (1) to (8), wherein the pattern image includes a plurality of the first images regularly arranged at specific intervals, and the medical image processing device further includes pattern image generation circuitry configured to generate the pattern image, and pattern image controller configured to control an operation of the pattern image generation circuitry to change the specific intervals between the first images in the pattern image.

(10) The medical image processing device according to (9), wherein the pattern image controller is configured to change the specific intervals between the first images in the pattern image on the basis of a state of a medical observation device.

(11) The medical image processing device according to (9), wherein the pattern image controller is configured to make an interval between the first images located in a first area in the pattern image different from an interval between the first images located in a second area different from the first area in the pattern image.

(12) The medical image processing device according to (9), wherein the pattern image controller is configured to change the specific intervals between the first images in the pattern image on the basis of a specific feature portion in a subject included in the captured image.

(13) The medical image processing device according to any one of (1) to (12), further including a display controller configured to output, to a display device for displaying an image, a video signal according to an image for display, the video signal including the captured image and the superimposed image.

(14) The medical image processing device according to any one of (1) to (12), further including: a display controller configured to output, to a display device for displaying an image, a video signal according to an image for display; pattern image generation circuitry configured to generate each of a first pattern image that is the pattern image and a second pattern image that is the pattern image; and a pattern image controller configured to control an operation of the pattern image generation circuitry, wherein the pattern image controller is configured to perform control to extract a first range having a specific first feature in the captured image, generate the first pattern image in which the first images located at a position corresponding to the first range in the first pattern image are distinguishable from the other first images, extract a second range having a specific second feature in the captured image, and generate the second pattern image in which the first images located at a position corresponding to the second range in the second pattern image are distinguishable from the other first images, the superimposed image generation circuitry is configured to generate a first superimposed image that is the superimposed image in which the first pattern image and the captured image are superimposed on each other, and generate a second superimposed image that is the superimposed image in which the second pattern image and the captured image are superimposed on each other, and the display controller is configured to output, to the display device, the video signal according to the image for display including the first superimposed image and the second superimposed image.

(15) The medical image processing device according to any one of (1) to (14), wherein the first image includes at least two types of a second image and a third image different from the second image.

(16) The medical image processing device according to any one of (1) to (15), wherein the first image is a dot.

(17) The medical image processing device according to any one of (1) to (15), wherein the first image has a frame shape, and the pattern image is a mesh-like image in which the first images are arranged in parallel in a specific pattern.

(18) A medical observation system including: a medical observation device configured to capture an image of a subject; and a medical image processing device configured to process image information obtained by imaging with the medical observation device, the medical image processing device including image acquisition circuitry configured to acquire the image information, and superimposed image generation circuitry configured to generate a superimposed image in which a pattern image having first images with a specific shape arranged in parallel in a specific pattern and a captured image based on the image information are superimposed on each other.

The medical image processing device and the medical observation system according to the present disclosure improve convenience.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising:
   a pattern image generation circuitry configured to
      generate a pattern image having first images with a specific shape arranged in parallel in a specific pattern,
      select first images in a specific area in the pattern image,
      generate a first pattern image in which the first images located at a position corresponding to the specific area in the first pattern image are distinguishable from other first images, the first pattern image including distinguishable first images and the other first images;
   superimposed image generation circuitry configured to generate a first superimposed image in which the first pattern image and a captured image based on image information obtained by imaging with a medical observation device are superimposed on each other; and
   a display control circuitry configured to output, to a display device for displaying an image, a video signal according to the image for display, wherein
   the pattern image generation circuitry configured to:
      extract a first range having a specific first feature in the captured image as the specific area to generate the first pattern image,
      extract a second range having a specific second feature in the captured image, and
      generate a second pattern image in which the first images located at a position corresponding to the second range in the second pattern image are distinguishable from the other first images;
   the superimposed image generation circuitry is configured to
      generate a second superimposed image that is the superimposed image in which the second pattern image and the captured image are superimposed on each other; and
   the display control circuitry is configured to output, to the display device, the video signal according to the image for display including the first superimposed image and the second superimposed image.

2. The medical image processing device according to claim 1, wherein the pattern image generation circuitry is configured to generate the first pattern image in which the distinguishable first images are distinguishable from the other first images by changing an overall appearance of the distinguishable first images without changing a shape of the distinguishable first images and a shape of the other first images.

3. The medical image processing device according to claim 1, wherein the pattern image generation circuitry is configured to generate the first pattern image in which the distinguishable first images are distinguishable from the other first images by changing a partial appearance of all of the distinguishable first images without changing a shape of the distinguishable first images and a shape of the other first images.

4. The medical image processing device according to claim 1, wherein the pattern image generation circuitry is configured to generate the first pattern image in which the distinguishable first images are distinguishable from the other first images by changing at least one of brightness and color of the distinguishable first images and transmittance to the captured image.

5. The medical image processing device according to claim 1, wherein the pattern image generation circuitry is configured to extract an area having a specific feature from the captured image as the specific area.

6. The medical image processing device according to claim 1, wherein the pattern image generation circuitry is configured to use a position corresponding to a preset area in the pattern image as the specific area.

7. The medical image processing device according to claim 6, wherein the pattern image generation circuitry is configured to generate the first pattern image in which the distinguishable first images are distinguishable from the other first images by making an overall appearance of the distinguishable first images less visible with respect to the other first images without changing a shape of the distinguishable first images and a shape of the other first images.

8. The medical image processing device according to claim 1, wherein
the pattern image includes a plurality of the first images regularly arranged at specific intervals, and
the pattern image generation circuitry is configured to change the specific intervals between the first images in the pattern image to generate the first pattern image.

9. The medical image processing device according to claim 8, wherein the pattern image generation circuitry is configured to change the specific intervals between the first images in the first pattern image on the basis of a state of a medical observation device.

10. The medical image processing device according to claim 8, wherein the pattern image generation circuitry is configured to make an interval between the first images located in a first area in the first pattern image different from an interval between the first images located in a second area different from the first area in the first pattern image.

11. The medical image processing device according to claim 8, wherein the pattern image generation circuitry is configured to change the specific intervals between the first images in the first pattern image on the basis of a specific feature portion in a subject included in the captured image.

12. The medical image processing device according to claim 1, wherein the video signal includes the captured image and the first superimposed image.

13. The medical image processing device according to claim 1, wherein the first image includes at least two types of a second image and a third image different from the second image.

14. The medical image processing device according to claim 1, wherein the first image is a dot.

15. The medical image processing device according to claim 1, wherein
the first image has a frame shape, and
the pattern image is a mesh-like image in which the first images are arranged in parallel in a specific pattern.

16. A medical observation system comprising:
a medical observation device configured to capture an image of a subject;
a medical image processing device configured to process image information obtained by imaging with the medical observation device, the medical image processing device including:
image acquisition circuitry configured to acquire the image information;
a pattern image generation circuitry configured to
generate a pattern image having first images with a specific shape arranged in parallel in a specific pattern,
select first images in a specific area in the pattern image,
generate a first pattern image in which the first images located at a position corresponding to the specific area in the first pattern image are distinguishable from the other first images;
superimposed image generation circuitry configured to generate a superimposed image in which the first pattern image and a captured image based on the image information are superimposed on each other; and
a display control circuitry configured to output, to a display device for displaying an image, a video signal according to the image for display, wherein
the pattern image generation circuitry configured to:
extract a first range having a specific first feature in the captured image as the specific area to generate the first pattern image,
extract a second range having a specific second feature in the captured image, and
generate a second pattern image in which the first images located at a position corresponding to the second range in the second pattern image are distinguishable from the other first images,
the superimposed image generation circuitry is configured to generate a second superimposed image that is the superimposed image in which the second pattern image and the captured image are superimposed on each other, and
the display control circuitry is configured to output, to the display device, the video signal according to the image for display including the first superimposed image and the second superimposed image.

17. A non-transitory computer readable storage device having computer readable instructions that when executed by circuitry cause the circuitry to:
generate a pattern image having first images with a specific shape arranged in parallel in a specific pattern;
select first images in a specific area in the pattern image;
generate a first pattern image in which the first images located at a position corresponding to the specific area in the first pattern image are distinguishable from the other first images;
generate a first superimposed image in which the first pattern image and a captured image based on image information obtained by imaging with a medical observation device are superimposed on each other;
extract a first range having a specific first feature in the captured image as the specific area to generate the first pattern image;
extract a second range having a specific second feature in the captured image;
generate a second pattern image in which the first images located at a position corresponding to the second range in the second pattern image are distinguishable from the other first images; and
generate a second superimposed image that is the superimposed image in which the second pattern image and the captured image are superimposed on each other.

* * * * *